(12) United States Patent
Thissen

(10) Patent No.: US 11,642,114 B2
(45) Date of Patent: May 9, 2023

(54) STEERABLE INSTRUMENT COMPRISING A RADIAL SPACERS BETWEEN COAXIAL CYLINDRICAL ELEMENTS

(71) Applicant: Fortimedix Assets II B.V., Geleen (NL)

(72) Inventor: Mattheus Hendrik Louis Thissen, Swalmen (NL)

(73) Assignee: Fortimedix Assets II B.V., Geleen (NL)

( * ) Notice: Subject to any disclaimer, the term of this patent is extended or adjusted under 35 U.S.C. 154(b) by 651 days.

(21) Appl. No.: 16/626,343

(22) PCT Filed: Jul. 3, 2018

(86) PCT No.: PCT/NL2018/050430
§ 371 (c)(1),
(2) Date: Dec. 24, 2019

(87) PCT Pub. No.: WO2019/009710
PCT Pub. Date: Jan. 10, 2019

(65) Prior Publication Data
US 2020/0129166 A1 Apr. 30, 2020

(30) Foreign Application Priority Data
Jul. 4, 2017 (NL) ..................................... 2019175

(51) Int. Cl.
*A61B 17/00* (2006.01)
*A61B 17/29* (2006.01)

(52) U.S. Cl.
CPC ........ *A61B 17/00234* (2013.01); *A61B 17/29* (2013.01); *A61B 2017/00309* (2013.01);
(Continued)

(58) Field of Classification Search
CPC .......... A61M 25/0133; A61M 25/0138; A61M 25/0141; A61M 25/0147;
(Continued)

(56) References Cited

U.S. PATENT DOCUMENTS

| 6,107,004 A | 8/2000 | Donadio, III |
| 2006/0281566 A1 | 12/2006 | Lee |

(Continued)

FOREIGN PATENT DOCUMENTS

| DE | 102009037030 A1 | 2/2011 |
| DE | 102010000787 A1 | 7/2011 |

(Continued)

*Primary Examiner* — Majid Jamialahmadi
(74) *Attorney, Agent, or Firm* — N.V. Nederlandsch Octrooibureau

(57) ABSTRACT

A steerable instrument has an actuator at a proximal side and a bendable zone at a distal side. The actuator controls bending of the flexible zone by means of one or more longitudinal elements. The instrument has a first cylindrical element, a second cylindrical element and a third cylindrical element. The second cylindrical element has a zone with a longitudinal element portion with a first height in a radial direction of the instrument. Radial spacers are located at mutual sides of the longitudinal element portion, which have, at least locally, a second height in the radial direction larger than the first height.

15 Claims, 16 Drawing Sheets

(52) U.S. Cl.
CPC ............... *A61B 2017/00327* (2013.01); *A61B 2017/00526* (2013.01); *A61B 2017/2906* (2013.01); *A61B 2017/2908* (2013.01)

(58) Field of Classification Search
CPC . A61M 2025/0161; A61B 2017/00309; A61B 2017/00305; A61B 2017/00318; A61B 2017/00526
See application file for complete search history.

(56) References Cited

U.S. PATENT DOCUMENTS

| | | |
|---|---|---|
| 2009/0069632 A1 | 3/2009 | McIntyre et al. |
| 2015/0107396 A1 | 4/2015 | Suehara |
| 2015/0112134 A1 | 4/2015 | Suehara et al. |
| 2016/0015249 A1 | 1/2016 | Suehara |
| 2018/0008805 A1* | 1/2018 | Pleijers ................. A61B 17/29 |

FOREIGN PATENT DOCUMENTS

| | | |
|---|---|---|
| DE | 102010005243 A1 | 7/2011 |
| WO | 97/42910 A1 | 11/1997 |
| WO | 03/037416 A1 | 5/2003 |
| WO | 2006/026520 A2 | 8/2005 |
| WO | 2009/098244 A2 | 2/2008 |
| WO | 2009/112060 A1 | 9/2009 |
| WO | 2009/127236 A1 | 10/2009 |
| WO | 2010/028090 A2 | 3/2010 |
| WO | 2010/105649 A1 | 9/2010 |
| WO | 2010/136272 A1 | 12/2010 |
| WO | 2010/136274 A1 | 12/2010 |
| WO | 2010/151698 A2 | 12/2010 |
| WO | 2011/018179 A2 | 2/2011 |
| WO | 2011/079897 A2 | 7/2011 |
| WO | 2012/128618 A1 | 9/2012 |
| WO | 2012/139869 A2 | 10/2012 |
| WO | 2012/151396 A2 | 11/2012 |
| WO | 2012/173478 A1 | 12/2012 |
| WO | 2014/011049 A1 | 1/2014 |
| WO | 2015/084174 A1 | 6/2015 |
| WO | 2015/085307 A1 | 6/2015 |
| WO | 2016/030457 A1 | 3/2016 |
| WO | 2016/061291 A1 | 4/2016 |
| WO | 2016/089202 A1 | 6/2016 |
| WO | 2016/091856 A1 | 6/2016 |
| WO | 2016/091858 A1 | 6/2016 |
| WO | 2016/138443 A2 | 9/2016 |
| WO | 2016/160694 A1 | 10/2016 |
| WO | 2016/172706 A1 | 10/2016 |
| WO | 2017/010883 A2 | 1/2017 |
| WO | 2017/014624 A1 | 1/2017 |
| WO | 2017/082720 A1 | 5/2017 |
| WO | 2017/176766 A1 | 10/2017 |
| WO | 2017/213491 A1 | 12/2017 |
| WO | 2018/067004 A1 | 4/2018 |
| WO | 2019/009710 A1 | 1/2019 |
| WO | 2019/096932 A1 | 5/2019 |
| WO | 2019/139811 A1 | 7/2019 |

\* cited by examiner

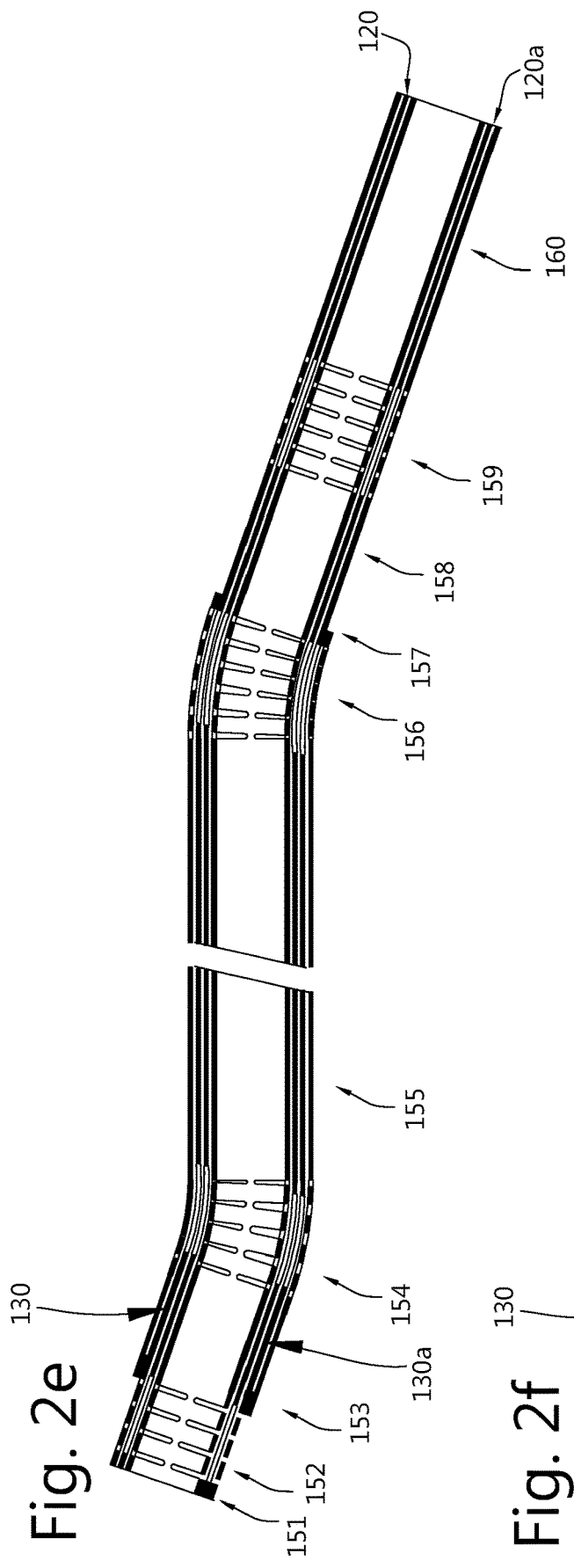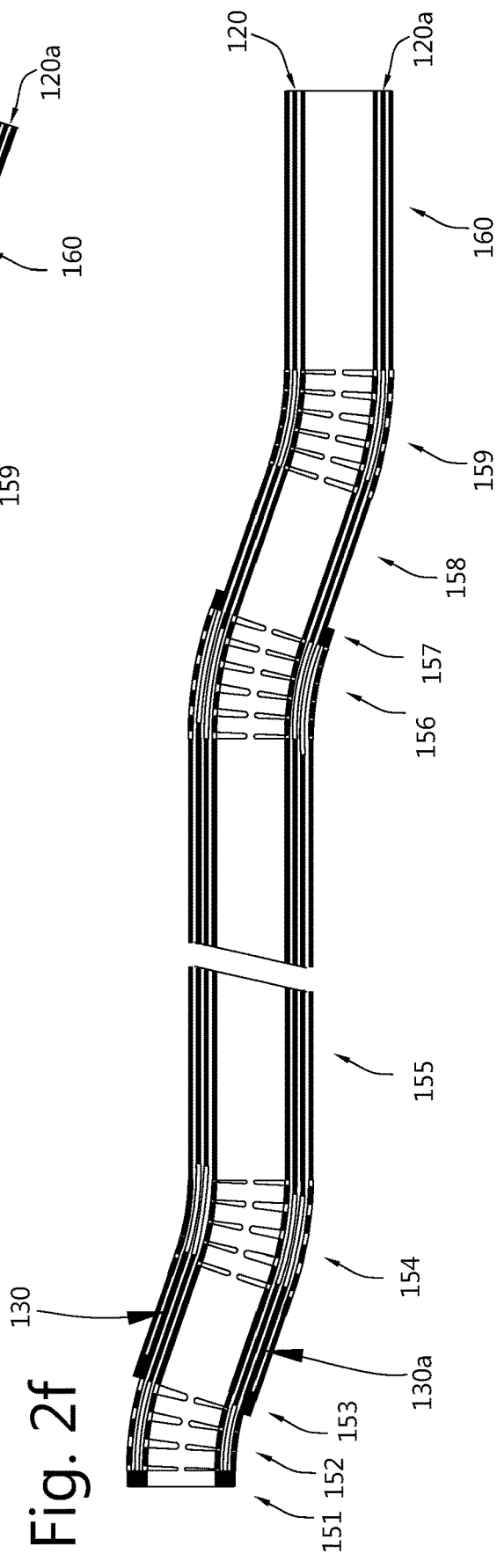

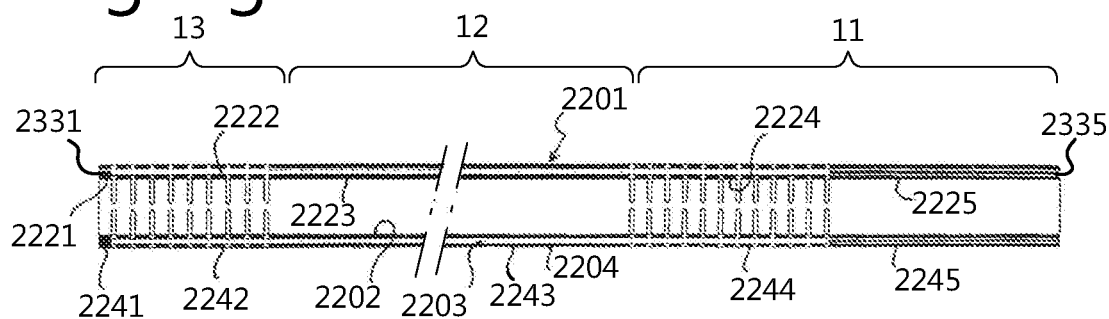
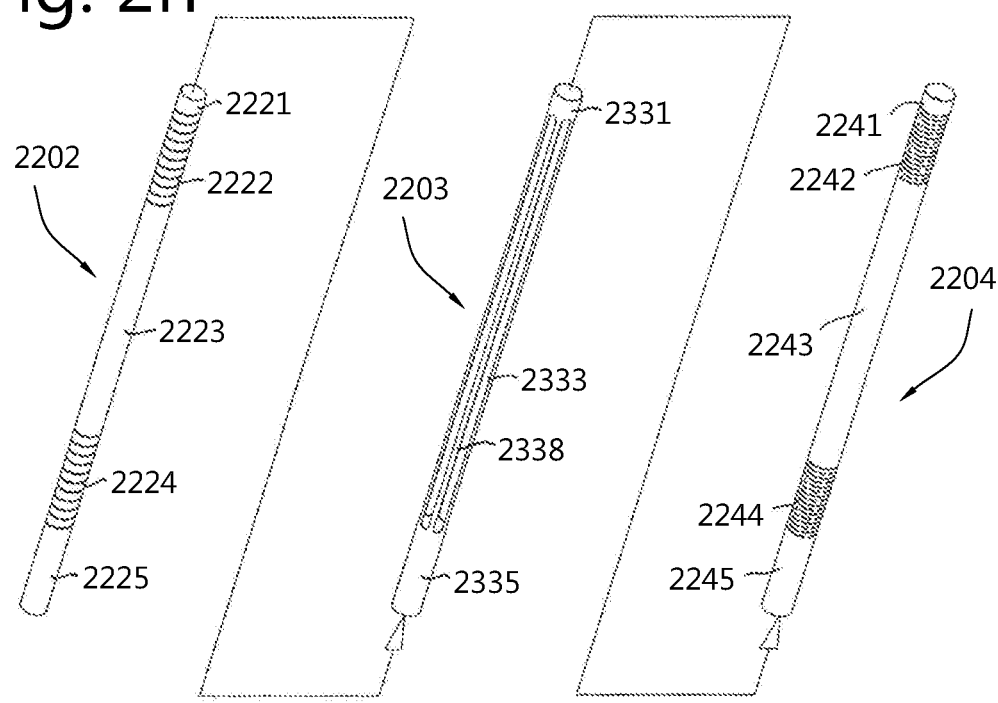
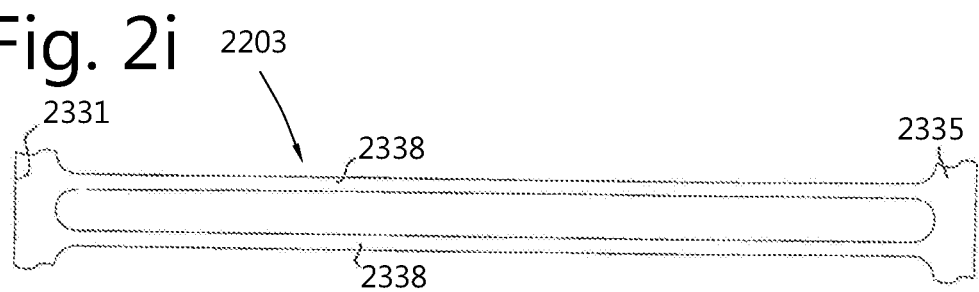

STEERABLE INSTRUMENT COMPRISING A RADIAL SPACERS BETWEEN COAXIAL CYLINDRICAL ELEMENTS

FIELD OF THE INVENTION

The present invention relates to a steerable instrument for endoscopic and/or invasive type of applications, such as in surgery. The steerable instrument according to the invention can be used in both medical and non-medical applications. Examples of the latter include inspection and/or repair of mechanical and/or electronic hardware at locations that are difficult to reach. Hence, terms used in the following description such as endoscopic application or invasive instrument, must be interpreted in a broad manner.

BACKGROUND ART

Transformation of surgical interventions that require large incisions for exposing a target area into minimal invasive surgical interventions, i.e. requiring only natural orifices or small incisions for establishing access to the target area, is a well-known and ongoing process. In performing minimal invasive surgical interventions, an operator such as a physician, requires an access device that is arranged for introducing and guiding invasive instruments into the human or animal body via an access port of that body. In order to reduce scar tissue formation and pain to a human or animal patient, the access port is preferably provided by a single small incision in the skin and underlying tissue. In that respect the possibility to use a natural orifice of the body would even be better. Furthermore, the access device preferably enables the operator to control one or more degrees of freedom that the invasive instruments offer. In this way, the operator can perform required actions at the target area in the human or animal body in an ergonomic and accurate manner with a reduced risk of clashing of the instruments used.

Surgical invasive instruments and endoscopes through which these instruments are guided towards the target area are well-known in the art. Both the invasive instruments and endoscopes can comprise a steerable tube that enhances its navigation and steering capabilities. Such a steerable tube preferably comprises a proximal end part including at least one flexible zone, a distal end part including at least one flexible zone, and a rigid intermediate part, wherein the steerable tube further comprises a steering arrangement that is adapted for translating a deflection of at least a part of the proximal end part relative to the rigid intermediate part into a related deflection of at least a part of the distal end part.

Furthermore, the steerable tube preferably comprises a number of co-axially arranged cylindrical elements including an outer element, an inner element and one or more intermediate elements depending on the number of flexible zones in the proximal and distal end parts of the tube and the desired implementation of the steering members of the steering arrangement, i.e. all steering members can be arranged in a single intermediate element or the steering members are divided in different sets and each set of steering members is arranged in a different intermediate member. In most prior art devices, the steering arrangement comprises conventional steering cables with, for instance, sub 1 mm diameters as steering members, wherein the steering cables are arranged between related flexible zones at the proximal and distal end parts of the tube. However, as steering cables have many well-known disadvantages, it is preferred to avoid them and to implement the steering members by one or more sets of longitudinal elements that form integral parts of the one or more intermediate elements. Each of the intermediate elements can be fabricated either by using a suitable material addition technique, such as injection moulding or plating, or by starting from a cylindrical element and then using a suitable material removal technique, such as laser cutting, photochemical etching, deep pressing, conventional chipping techniques such as drilling or milling or high-pressure water jet cutting systems. Of the aforementioned material removal techniques, laser cutting is very advantageous as it allows a very accurate and clean removal of material under reasonable economic conditions. Further details regarding the design and fabrication of the above-mentioned steerable tube and the steering arrangement thereof have been described for example in WO 2009/112060 A1, WO 2009/127236 A1, U.S. Ser. No. 13/160,949, and U.S. Ser. No. 13/548,935 of the applicant, all of which are hereby incorporated by reference in their entirety.

Steerable invasive instruments typically comprise a handle that is arranged at the proximal end part of the steerable tube for steering the tube and/or for manipulating a tool that is arranged at the distal end part of the steerable tube. Such a tool can for example be a camera, a manual manipulator, e.g. a pair of scissors, forceps, or manipulators using an energy source, e.g. an electrical, ultrasonic or optical energy source.

In this application, the terms "proximal" and "distal" are defined with respect to an operator, e.g. a physician that operates the instrument or endoscope. For example, a proximal end part is to be construed as a part that is located near the physician and a distal end part as a part located at a distance from the physician.

In these steerable instruments, the longitudinal elements (or steering wires) need be flexible in at least those portions of the instrument that should allow bending relative to the longitudinal axis of the instrument, both at the proximal end and distal end. These longitudinal elements are often located between an adjacent outer and adjacent inner cylindrical element. When bending these flexible zones of the instrument, in each such zone these longitudinal elements bend together with bendable portions of the outer and inner cylindrical element. However, sometimes the bending of such zone causes the bending outer and bending inner cylindrical element to clamp the longitudinal element between the outer and inner cylindrical elements such that it is difficult to move the longitudinal elements any further in the longitudinal direction. This effect may also be caused/increased by different longitudinal elements arranged on top of each other in the bendable portions.

SUMMARY OF THE INVENTION

It is an object of the invention to provide a steerable instrument for endoscopic and/or invasive type of applications which prevents such clamping to occur when bending the instrument.

This is achieved by a steerable instrument as claimed in claim 1.

The steerable instrument may be manufactured by a method as claimed in the independent method claim.

Embodiments of the invention are claimed in dependent claims.

The steerable instrument according to the invention solves the above mentioned problem of clamping.

BRIEF DESCRIPTION OF THE DRAWINGS

Further features and advantages of the invention will become apparent from the description of the invention by way of non-limiting and non-exclusive embodiments. These embodiments are not to be construed as limiting the scope of protection. The person skilled in the art will realize that other alternatives and equivalent embodiments of the invention can be conceived and reduced to practice without departing from the scope of the present invention. Embodiments of the invention will be described with reference to the figures of the accompanying drawings, in which like or same reference symbols denote like, same or corresponding parts, and in which:

FIG. 2*h* shows a perspective view of a part of the elongated tubular body as shown in FIG. 2*b*, wherein the outer cylindrical element partially has been removed to show an exemplary embodiment of the longitudinal steering elements that have been obtained after providing longitudinal slits to the wall of an intermediate cylindrical element that interconnects the first proximal flexible zone and the first distal flexible zone of the elongated tubular body.

DESCRIPTION OF EMBODIMENTS

Figure 1:
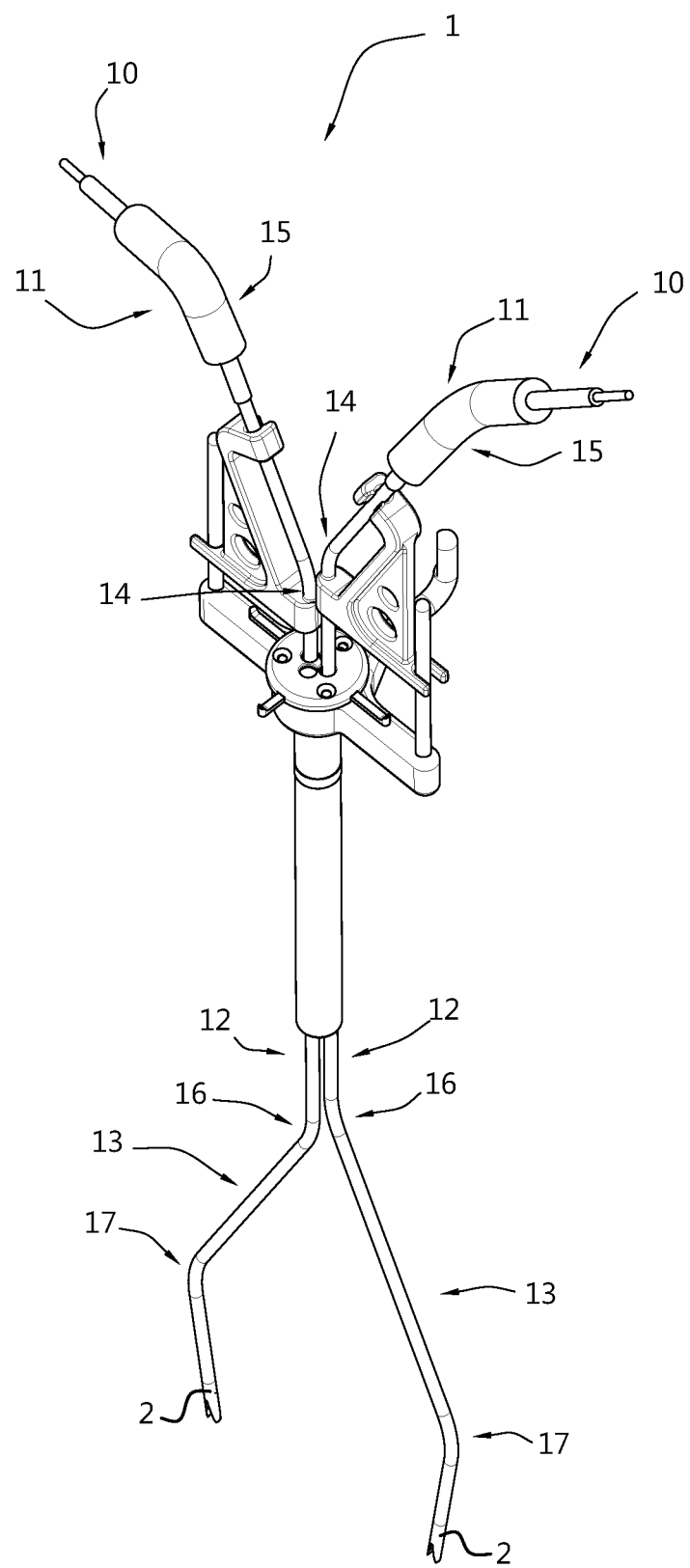
FIG. 1 shows a schematic perspective view of an invasive instrument assembly having two steerable instruments.
Figure 2A:
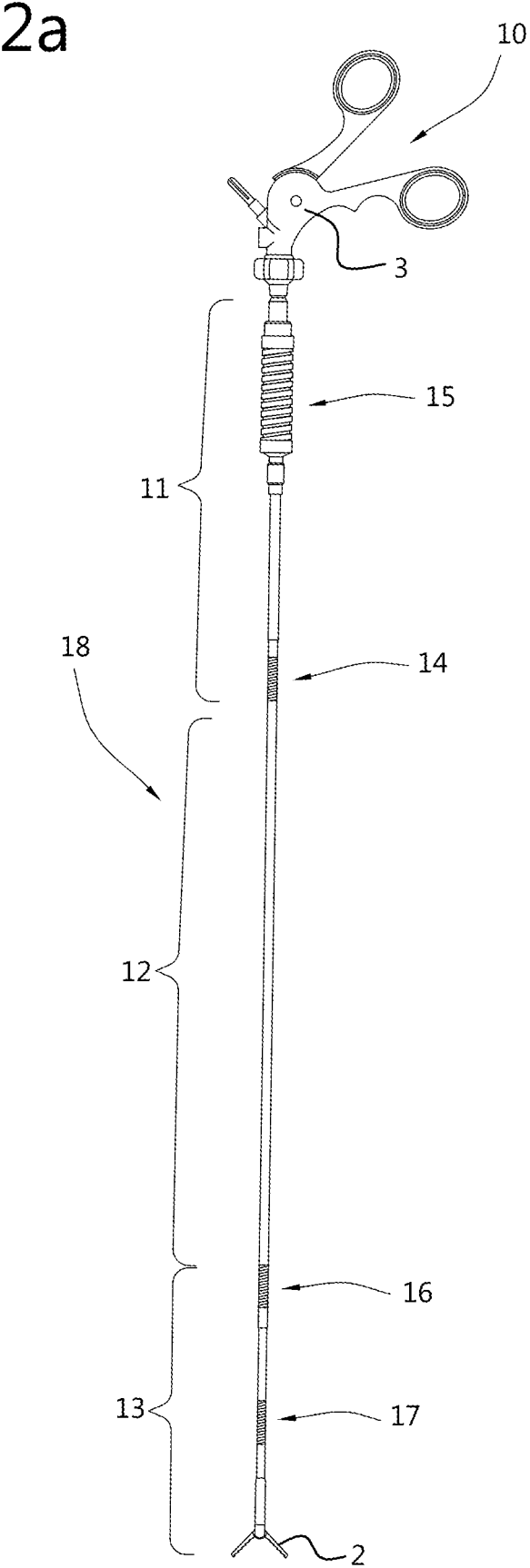
FIG. 2*a* shows a side view of a non-limiting embodiment of a steerable invasive instrument.

FIG. 2*a* shows a non-limiting embodiment of a steerable invasive instrument 10. FIG. 1 shows a non-limiting embodiment of an invasive instrument assembly 1 having an introducer with two such steerable invasive instruments 10. Details of the steerable invasive instruments 10 are explained in relation to FIGS. 2*b* to 2*j*.

FIG. 2*a* shows a side view of the steerable invasive instrument 10. The steerable instrument 10 comprises an elongated tubular body 18 having a proximal end part 11 including two actuation flexible zones 14, 15, a distal end part 13 including two distal flexible zones 16, 17, and a rigid intermediate part 12. The actuation flexible zones 14, 15 in the present embodiment are configured as flexible proximal zones, and will further be referred to as flexible proximal zones. These flexible proximal zones 14, 15 are connected to the distal flexible zones by suitable longitudinal elements (not shown in FIG. 2*a*). By bending one such proximal flexible zone 14, 15, respectively, a corresponding flexible distal zone will also bend, as will be explained in detail hereinafter. The rigid intermediate part may also have one more bendable zones. However, these bendable zones are just flexible and their bending is not controlled by another bendable zone. If desired, more than two steerable flexible distal zones can be provided. At the distal end part 13 a tool, like a forceps 2 is arranged. At the proximal end part 11 a handle 3 is arranged that is adapted for opening and closing the jaw of the forceps 2 via, e.g., a suitable cable (not shown) arranged within the instrument. Cable arrangements for doing so are well known in the art.

Figure 2B:
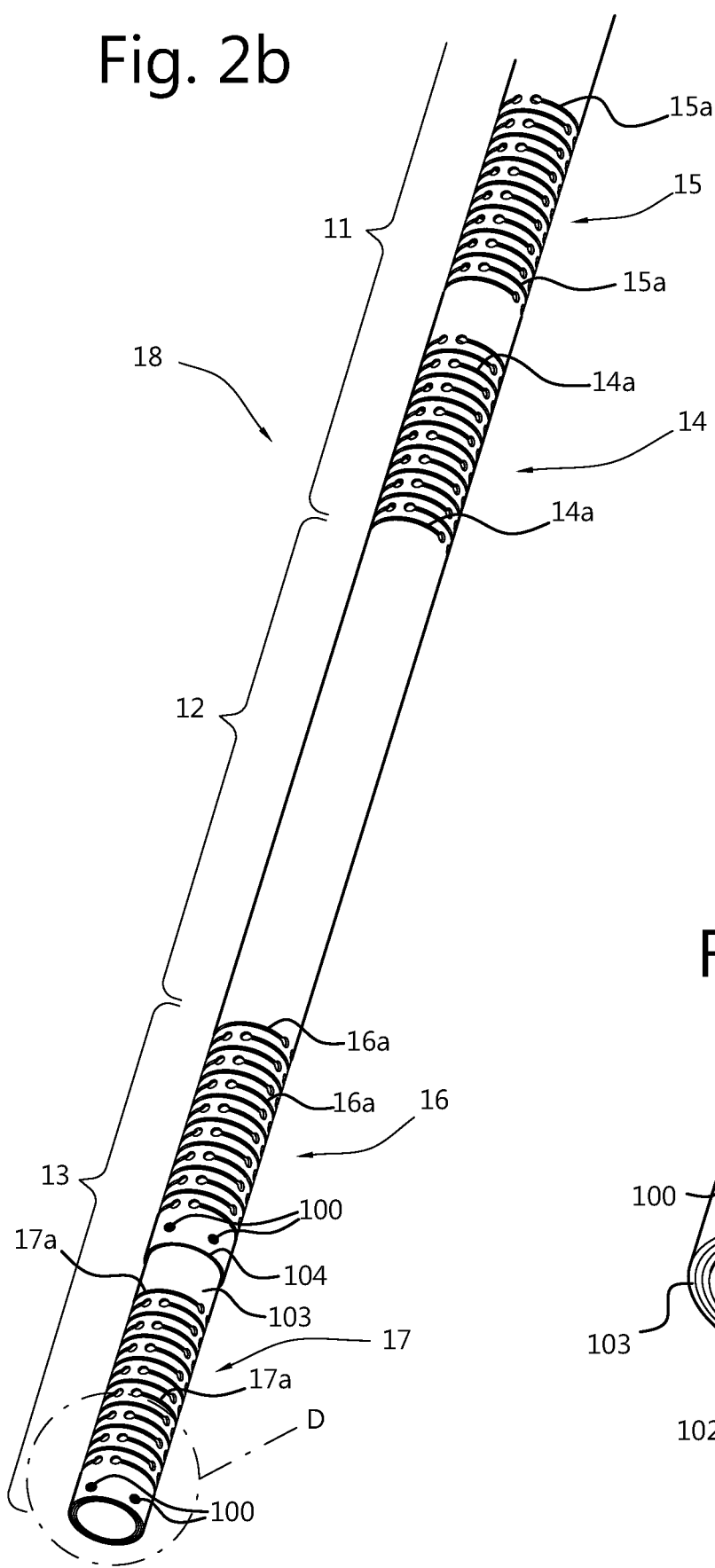
FIG. 2*b* provides a detailed perspective view of a non-limiting embodiment of the elongated tubular body of the steerable instrument.

FIG. 2*b* provides a detailed perspective view of the distal portion of the elongated tubular body 18 of the steerable instrument 10 and shows that the elongated tubular body 18 comprises of a number of co-axially arranged layers or cylindrical elements including an outer cylindrical element 104 that ends after the first distal flexible zone 16 at the distal end portion 13. The distal end portion 13 of the outer cylindrical element 104 is fixedly attached to the cylindrical element 103 located within and adjacent to the outer cylindrical element 104, e.g. by means of spot welding at welding spots 100. However, any other suitable attachment method can be used, including any mechanical snap fit connection or gluing by a suitable glue.

Figure 2C:
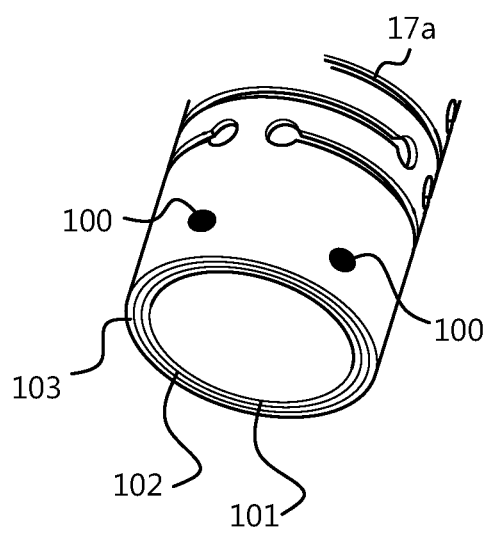
FIG. 2*c* provides a more detailed view of the distal end part of the elongated tubular body as shown in FIG. 2*b*.

FIG. 2*c* provides a more detailed view of the distal end part 13 and shows that it includes three co-axially arranged layers or cylindrical elements being an inner cylindrical element 101, a first intermediate cylindrical element 102 and a second intermediate cylindrical element 103. The distal ends of inner cylindrical element 101, first intermediate cylindrical element 102 and second intermediate cylindrical element 103 are all three fixedly attached to one another. This may be done by means of spot welding at welding spots 100. However, any other suitable attachment method can be used, including any mechanical snap fit connection or gluing by a suitable glue. The points of attachment may be at the end edges of inner cylindrical element 101, first intermediate cylindrical element 102 and second intermediate cylindrical element 103, as shown in the figures. However, these points of attachment may also be located some distance away from these edges, be it, preferably, between the end edges and the locations of the flexible zone 17.

It will be clear to the skilled person that the elongated tubular body 18 as shown in FIG. 2*b* comprises four cylindrical elements in total. The elongated tubular body 18 according to the embodiment shown in FIG. 2*b* comprises two intermediate cylindrical elements 102 and 103 in which the steering members of the steering arrangement are arranged. The steering arrangement in the exemplary embodiment of the elongated tubular body 18 as shown in FIG. 2*b* comprises the two flexible zones 14, 15 at the proximal end part 11 of the elongated tubular body 18, the two flexible zones 16, 17 at the distal end part 13 of the elongated tubular body 18 and the steering members that are arranged between related flexible zones at the proximal 11 and distal 13 end parts. An exemplary actual arrangement of the steering members is shown in FIG. 2*d*, which provides a schematic longitudinal cross-sectional view of the exemplary embodiment of the elongated tubular body 18 as shown in FIG. 2*b*.

Figure 2D:
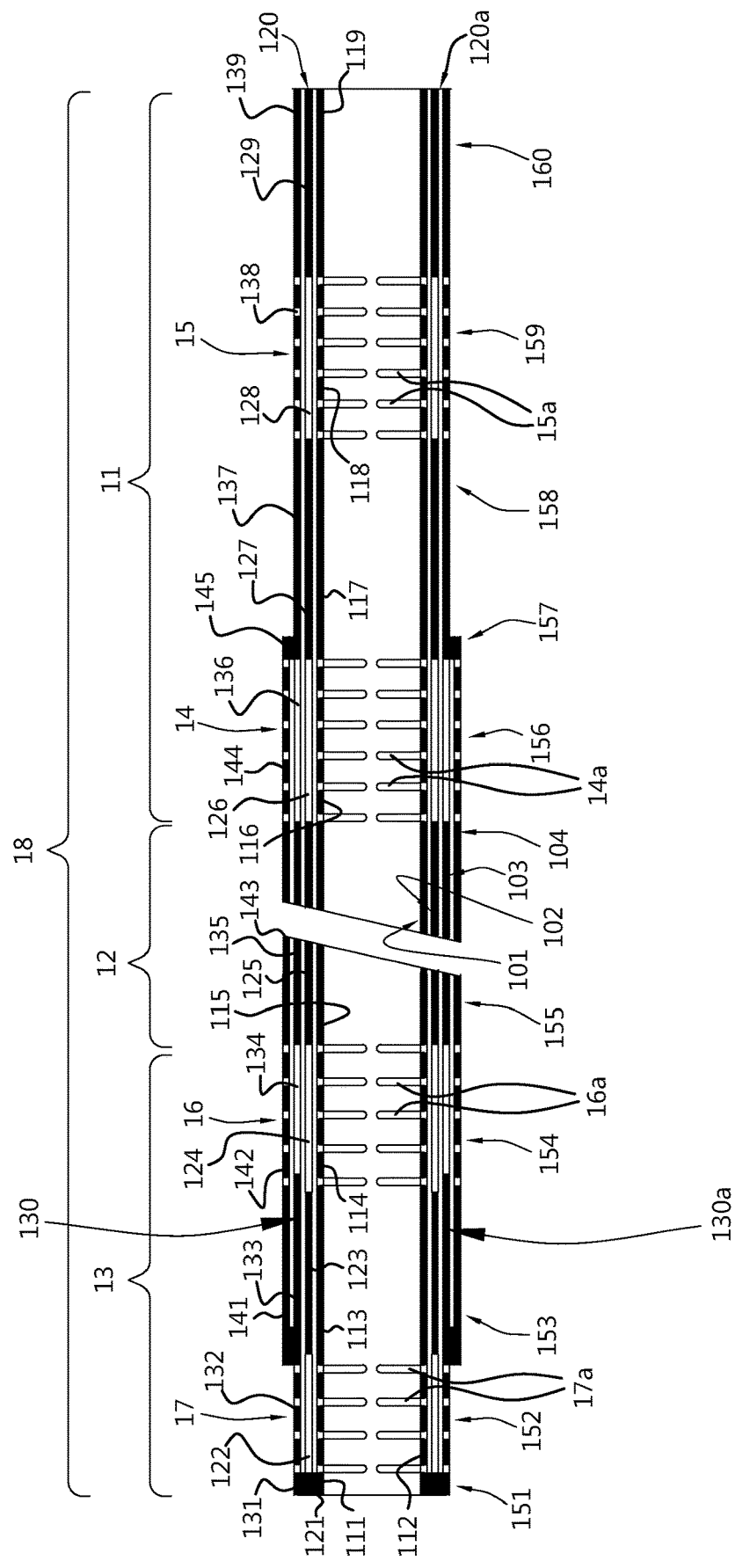
FIG. 2*d* shows a longitudinal cross-sectional view of the elongated tubular body of the steerable instrument as shown in FIG. 2*b*.

FIG. 2*d* shows a cross section of the four layers or cylindrical elements mentioned above, i.e. the inner cylindrical element 101, the first intermediate cylindrical element 102, the second intermediate cylindrical element 103, and the outer cylindrical element 104.

The inner cylindrical element 101, as seen along its length from the distal end to the proximal end of the instrument, comprises a rigid ring 111, which is arranged at the distal end part 13 of the steerable instrument 10, a first flexible portion 112, a first intermediate rigid portion 113, a second flexible portion 114, a second intermediate rigid portion 115, a third flexible portion 116, a third intermediate rigid portion 117, a fourth flexible portion 118, and a rigid end portion 119, which is arranged at the proximal end portion 11 of the steerable instrument 10.

The first intermediate cylindrical element 102, as seen along its length from the distal end to the proximal end of the instrument, comprises a rigid ring 121, a first flexible portion 122, a first intermediate rigid portion 123, a second flexible portion 124, a second intermediate rigid portion 125, a third flexible portion 126, a third intermediate rigid portion 127, a fourth flexible portion 128, and a rigid end portion 129. The portions 122, 123, 124, 125, 126, 127 and 128 together form a longitudinal element 120 that can be moved in the longitudinal direction like a wire. The longitudinal dimensions of the rigid ring 121, the first flexible portion 122, the first intermediate rigid portion 123, the second flexible portion 124, the second intermediate rigid portion 125, the third flexible portion 126, the third intermediate rigid portion 127, the fourth flexible portion 128, and the rigid end portion 129 of the first intermediate element 102, respectively, are aligned with, and preferably approximately equal to the longitudinal dimensions of the rigid ring 111, the first flexible portion 112, the first intermediate rigid portion 113, the second flexible portion 114, the second intermediate rigid portion 115, the third flexible portion 116, the third intermediate rigid portion 117, the fourth flexible portion 118, and the rigid end portion 119 of the inner cylindrical element 101, respectively, and are coinciding with these portions as well. In this description "approximately equal" means that respective same dimensions are equal within a margin of less than 10%, preferably less than 5%.

Similarly, the first intermediate cylindrical element 102 comprises one or more other longitudinal elements of which one is shown with reference number 120*a*.

The second intermediate cylindrical element 103, as seen along its length from the distal end to the proximal end of the instrument, comprises a first rigid ring 131, a first flexible portion 132, a second rigid ring 133, a second flexible portion 134, a first intermediate rigid portion 135, a first intermediate flexible portion 136, a second intermediate rigid portion 137, a second intermediate flexible portion 138, and a rigid end portion 139. The portions 133, 134, 135 and 136 together form a longitudinal element 130 that can be moved in the longitudinal direction like a wire. The longitudinal dimensions of the first rigid ring 131, the first flexible portion 132 together with the second rigid ring 133 and the second flexible portion 134, the first intermediate rigid portion 135, the first intermediate flexible portion 136, the second intermediate rigid portion 137, the second intermediate flexible portion 138, and the rigid end portion 139 of the second intermediate cylinder 103, respectively, are aligned with, and preferably approximately equal to the longitudinal dimensions of the rigid ring 111, the first flexible portion 112, the first intermediate rigid portion 113, the second flexible portion 114, the second intermediate rigid portion 115, the third flexible portion 116, the third intermediate rigid portion 117, the fourth flexible portion 118, and the rigid end portion 119 of the first intermediate element 102, respectively, and are coinciding with these portions as well.

Similarly, the second intermediate cylindrical element 103 comprises one or more other longitudinal elements of which one is shown with reference number 130*a*.

The outer cylindrical element 104, as seen along its length from the distal end to the proximal end of the instrument, comprises a first rigid ring 141, a first flexible portion 142, a first intermediate rigid portion 143, a second flexible portion 144, and a second rigid ring 145. The longitudinal dimensions of the first flexible portion 142, the first intermediate rigid portion 143 and the second flexible portion 144 of the outer cylindrical element 104, respectively, are aligned with, and preferably approximately equal to the longitudinal dimension of the second flexible portion 134, the first intermediate rigid portion 135 and the first intermediate flexible portion 136 of the second intermediate element 103, respectively, and are coinciding with these portions as well. The rigid ring 141 has approximately the same length as the rigid ring 133 and is fixedly attached thereto, e.g. by spot welding or gluing. Preferably, the rigid ring 145 overlaps with the second intermediate rigid portion 137 only over a length that is required to make an adequate fixed attachment between the rigid ring 145 and the second intermediate rigid portion 137, respectively, e.g. by spot welding or gluing. The rigid rings 111, 121 and 131 are attached to each other, e.g., by spot welding or gluing. This may be done at the end edges thereof but also at a distance of these end edges.

In an embodiment, the same may apply to the rigid end portions 119, 129 and 139, which can be attached together as well in a comparable manner. However, the construction may be such that the diameter of the cylindrical elements at the proximal portion is larger, or smaller, with respect to the diameter at the distal portion. In such embodiment the construction at the proximal portion differs from the one shown in FIG. 2*d*. As a result of the increase or decrease in diameter an amplification or attenuation is achieved, i.e., the bending angle of a flexible zone at the distal portion will be larger or smaller than the bending angle of a corresponding flexible portion at the proximal portion.

The inner and outer diameters of the cylindrical elements 101, 102, 103, and 104 are chosen in such a way at a same location along the elongated tubular body 18 that the outer diameter of inner cylindrical element 101 is slightly less than the inner diameter of the first intermediate cylindrical element 102, the outer diameter of the first intermediate cylindrical element 102 is slightly less than the inner diameter of the second intermediate cylindrical element 103 and the outer diameter of the second intermediate cylindrical element 103 is slightly less than the inner diameter of the outer cylindrical element 104, in such a way that a sliding movement of the adjacent cylindrical elements with respect to each other is possible. The dimensioning should be such that a sliding fit is provided between adjacent elements. A clearance between adjacent elements may generally be in the order of 0.02 to 0.1 mm, but depends on the specific application and material used. The clearance preferably is smaller than a wall thickness of the longitudinal elements to prevent an overlapping configuration thereof. Restricting the clearance to about 30% to 40% of the wall thickness of the longitudinal elements is generally sufficient.

As can be seen in FIG. 2d, flexible zone 14 of the proximal end part 11 is connected to the flexible zone 16 of the distal end part 13 by portions 134, 135 and 136, of the second intermediate cylindrical element 103, which form a first set of longitudinal steering members of the steering arrangement of the steerable instrument 10. Furthermore, flexible zone 15 of the proximal end part 11 is connected to the flexible zone 17 of the distal end part 13 by portions 122, 123, 124, 125, 126, 127, and 128 of the first intermediate cylindrical element 102, which form a second set of longitudinal steering members of the steering arrangement. The use of the construction as described above allows the steerable instrument 10 to be used for double bending. The working principle of this construction will be explained with respect to the examples shown in FIGS. 2e and 2f.

For the sake of convenience, as shown in FIGS. 2d, 2e and 2f, the different portions of the cylindrical elements 101, 102, 103, and 104 have been grouped into zones 151-160 that are defined as follows. Zone 151 comprises the rigid rings 111, 121, and 131. Zone 152 comprises the portions 112, 122, and 132. Zone 153 comprises the rigid rings 133 and 141 and the portions 113 and 123. Zone 154 comprises the portions 114, 124, 134 and 142. Zone 155 comprises the portions 115, 125, 135 and 143. Zone 156 comprises the portions 116, 126, 136 and 144. Zone 157 comprises the rigid ring 145 and the parts of the portions 117, 127, and 137 coinciding therewith. Zone 158 comprises the parts of the portions 117, 127, and 137 outside zone 157. Zone 159 comprises the portions 118, 128 and 138. Finally, zone 160 comprises the rigid end portions 119, 129 and 139.

In order to deflect at least a part of the distal end part 13 of the steerable instrument 10, it is possible to apply a bending force, in any radial direction, to zone 158. According to the examples shown in FIGS. 2e and 2f, zone 158 is bent downwards with respect to zone 155. Consequently, zone 156 is bent downwards. Because of the first set of steering members comprising portions 134, 135, and 136 of the second intermediate cylindrical element 103 that are arranged between the second intermediate rigid portion 137 and the second rigid ring 133, the downward bending of zone 156 is transferred by a longitudinal displacement of the first set of steering members into an upward bending of zone 154 with respect to zone 155. This is shown in both FIGS. 2e and 2f.

It is to be noted that the exemplary downward bending of zone 156, only results in the upward bending of zone 154 at the distal end of the instrument as shown in FIG. 2e. Bending of zone 152 as a result of the bending of zone 156 is prevented by zone 153 that is arranged between zones 152 and 154. When subsequently a bending force, in any radial direction, is applied to the zone 160, zone 159 is also bent. As shown in FIG. 2f, zone 160 is bent in an upward direction with respect to its position shown in FIG. 2e. Consequently, zone 159 is bent in an upward direction. Because of the second set of steering members comprising portions 122, 123, 124, 125, 126, 127 and 128 of the first intermediate cylindrical element 102 that are arranged between the rigid ring 121 and the rigid end portion 129, the upward bending of zone 159 is transferred by a longitudinal displacement of the second set of steering members into a downward bending of zone 152 with respect to its position shown in FIG. 2e.

FIG. 2f further shows that the initial bending of the instrument in zone 154 as shown in FIG. 2e will be maintained because this bending is only governed by the bending of zone 156, whereas the bending of zone 152 is only governed by the bending of zone 159 as described above. Due to the fact that zones 152 and 154 are bendable independently with respect to each other, it is possible to give the distal end part 13 of the steerable instrument 10 a position and longitudinal axis direction that are independent from each other. In particular the distal end part 13 can assume an advantageous S-like shape. The skilled person will appreciate that the capability to independently bend zones 152 and 154 with respect to each other, significantly enhances the maneuverability of the distal end part 13 and therefore of the steerable instrument 10 as a whole.

Obviously, it is possible to vary the lengths of the flexible portions shown in FIGS. 2d to 2f as to accommodate specific requirements with regard to bending radii and total lengths of the distal end part 13 and the proximal end part 11 of the steerable instrument 10 or to accommodate amplification or attenuation ratios between bending of at least a part of the proximal end part 11 and at least a part of the distal end part 13.

The steering members comprise one or more sets of longitudinal elements that form integral parts of the one or more intermediate cylindrical elements 102, 103. Preferably, the longitudinal elements comprise remaining parts of the wall of an intermediate cylindrical element 102, 103 after the wall of the intermediate cylindrical element 102, 103 has been provided with longitudinal slits that define the remaining longitudinal steering elements.

Further details regarding the fabrication of the latter longitudinal steering elements are provided with reference to FIGS. 2g to 2i regarding an exemplary embodiment of a steerable instrument that comprises only one flexible zone at both its proximal 11 and distal end 13 parts.

FIG. 2g shows a longitudinal cross-section of a steerable instrument 2201 comprising three co-axially arranged cylindrical elements, i.e. inner cylindrical element 2202, intermediate cylindrical element 2203 and outer cylindrical element 2204. Suitable materials to be used for making the cylindrical elements 2202, 2203, and 2204 include stainless steel, cobalt-chromium, shape memory alloy such as Nitinol®, plastic, polymer, composites or other cuttable material. Alternatively, the cylindrical elements can be made by a 3D printing process.

The inner cylindrical element 2202 comprises a first rigid end part 2221, which is located at the distal end part 13 of the instrument 2201, a first flexible part 2222, an intermediate rigid part 2223, a second flexible part 2224 and a second rigid end part 2225, which is located at the proximal end part 11 of the instrument 2201.

The outer cylindrical element 2204 also comprises a first rigid end part 2241, a first flexible part 2242, an intermediate rigid part 2243, a second flexible part 2244 and a second rigid end part 2245. The lengths of the different parts of the cylindrical elements 2202 and 2204 are substantially the same so that when the inner cylindrical element 2202 is inserted into the outer cylindrical element 2204, the different parts are positioned against each other.

The intermediate cylindrical element 2203 also has a first rigid end part 2331 and a second rigid end part 2335 which in the assembled condition are located between the corresponding rigid parts 2221, 2241 and 2225, 2245 respectively of the two other cylindrical elements 2202, 2204. The intermediate part 2333 of the intermediate cylindrical element 2203 comprises three or more separate longitudinal elements which can have different forms and shapes as will be explained below. After assembly of the three cylindrical elements 2202, 2203 and 2204 whereby the element 2202 is inserted in the element 2203 and the two combined elements 2202, 2203 are inserted into the element 2204, at least the first rigid end part 2221 of the inner cylindrical element 2202, the first rigid end part 2331 of the intermediate cylindrical element 2203 and the first rigid end part 2241 of the outer cylindrical element 2204 at the distal end of the instrument are attached to each other. In the embodiment shown in FIGS. 2g and 2h, also the second rigid end part 2225 of the inner cylindrical element 2202, the second rigid end part 2335 of the intermediate cylindrical element 2203 and the second rigid end part 2245 of the outer cylindrical element 2204 at the proximal end of the instrument are attached to each other such that the three cylindrical elements 2202, 2203, 2204 form one integral unit.

In the embodiment shown in FIG. 2h the intermediate part 2333 of intermediate cylindrical element 2203 comprises a number of longitudinal elements 2338 with a uniform cross-section so that the intermediate part 2333 has the general shape and form as shown in the unrolled condition of the intermediate cylindrical element 2203 in FIG. 2i. From FIG. 2i it also becomes clear that the intermediate part 2333 is formed by a number of over the circumference of the intermediate cylindrical part 2203 equally spaced parallel longitudinal elements 2338. Advantageously, the number of longitudinal elements 2338 is at least three, so that the instrument 2201 becomes fully controllable in any direction, but any higher number is possible as well. Preferably, the number of longitudinal elements 2338 is 6 or 8.

The production of such an intermediate part is most conveniently done by injection moulding or plating techniques or starting from a cylindrical tube with the desired inner and outer diameters and removing parts of the wall of the cylindrical tube required to end up with the desired shape of the intermediate cylindrical element 2203. However, alternatively, any 3D printing method can be used.

The removal of material can be done by means of different techniques such as laser cutting, photochemical etching, deep pressing, conventional chipping techniques such as drilling or milling, high pressure water jet cutting systems or any suitable material removing process available. Preferably, laser cutting is used as this allows for a very accurate and clean removal of material under reasonable economic conditions. The above mentioned processes are convenient ways as the member 2203 can be made so to say in one process, without requiring additional steps for connecting the different parts of the intermediate cylindrical element as required in the conventional instruments, where conventional steering cables must be connected in some way to the end parts. The same type of technology can be used for producing the inner and outer cylindrical elements 2202 and 2204 with their respective flexible parts 2222, 2224, 2242 and 2244.

Figure 2J:
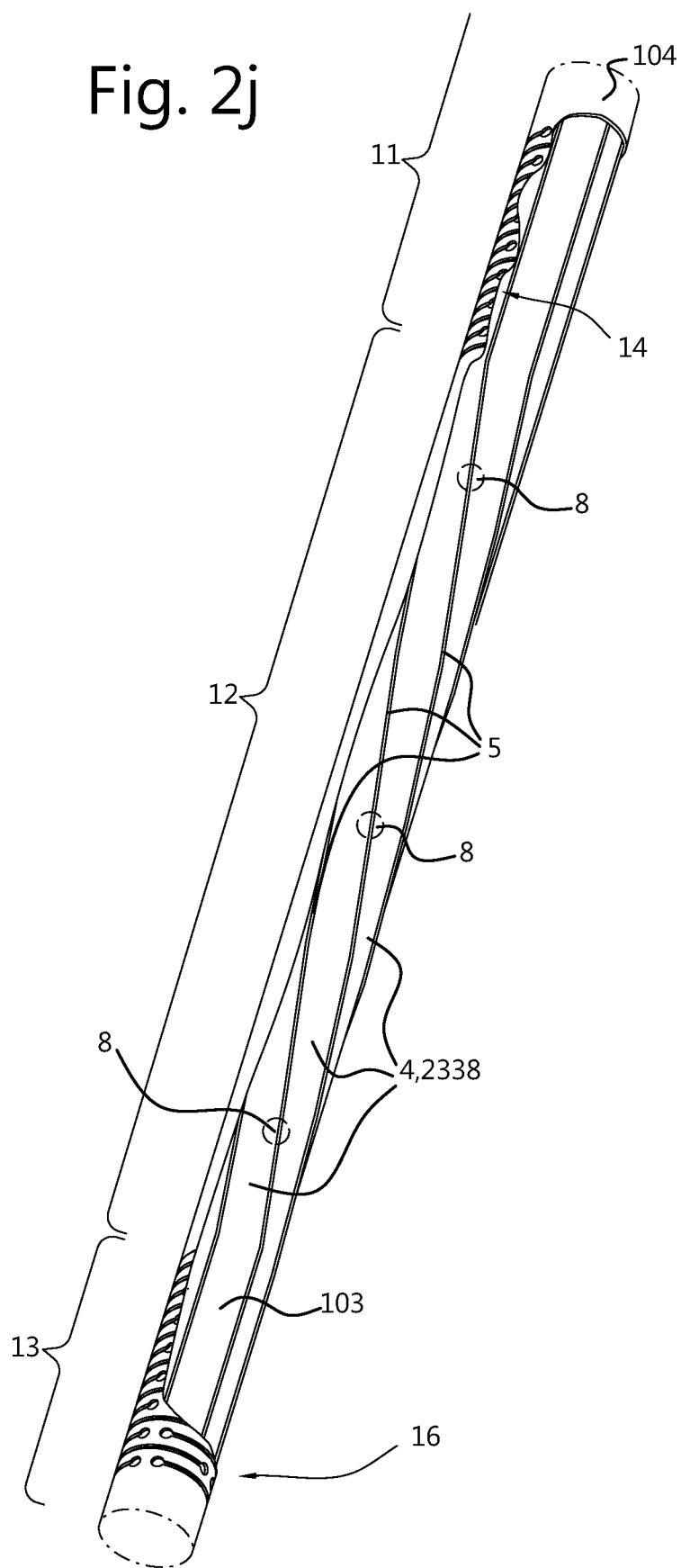
FIG. 2*e* shows a longitudinal cross-sectional view of the elongated tubular body of the steerable instrument as shown in FIG. 2*b*, wherein the first proximal and first distal flexible zones are bent, thereby illustrating the operation of the steering arrangement.
FIG. 2*f* shows a longitudinal cross-sectional view of the elongated tubular body of the steerable instrument as shown in FIG. 2*e*, wherein additionally the second proximal and second distal flexible zones are bent, thereby further illustrating the operation of the steering arrangement.
FIG. 2*g* shows a longitudinal cross-sectional view of an exemplary embodiment of a steerable instrument having one proximal and one distal flexible zone.
FIG. 2*h* shows a perspective exploded view of the three cylindrical elements of the steerable instrument shown in FIG. 2*g*.
FIG. 2*i* shows a top view of an unrolled version of an exemplary embodiment of the intermediate cylindrical element of the steerable instrument shown in FIG. 2*h*. The intermediate cylindrical element can be formed by rolling the unrolled version into a cylindrical configuration and attaching adjacent sides of the rolled-up configuration by any known attaching means such as by a welding technique.

FIG. 2j shows an exemplary embodiment of longitudinal (steering) elements 4 that have been obtained after providing longitudinal slits 5 to the wall of the second intermediate cylindrical element 103 that interconnects proximal flexible zone 14 and distal flexible zone 16 as described above. I.e., longitudinal steering elements 4 are, at least in part, spiraling about a longitudinal axis of the instrument such that an end portion of a respective steering element 4 at the proximal portion of the instrument is arranged at another angular orientation about the longitudinal axis than an end portion of the same longitudinal steering element 4 at the distal portion of the instrument. Were the longitudinal steering elements 4 arranged in a linear orientation, than a bending of the instrument at the proximal portion in a certain plane would result in a bending of the instrument at the distal portion in the same plane but in a 180 degrees opposite direction. This spiral construction of the longitudinal steering elements 4 allows for the effect that bending of the instrument at the proximal portion in a certain plane may result in a bending of the instrument at the distal portion in another plane, or in the same plane in the same direction. A preferred spiral construction is such that the end portion of a respective steering element 4 at the proximal portion of the instrument is arranged at an angularly shifted orientation of 180 degrees about the longitudinal axis relative to the end portion of the same longitudinal steering element 4 at the distal portion of the instrument. However, e.g. any other angularly shifted orientation, e.g. 90 degrees, is within the scope of this document. The slits are dimensioned such that movement of a longitudinal element is guided by adjacent longitudinal elements when provided in place in a steerable instrument.

The flexible portions 112, 132, 114, 142, 116, 144, 118, and 138 as shown in FIG. 2d, as well as the flexible parts 2222, 2224, 2242, and 2244 shown in FIGS. 2g and 2h can be obtained by the methods described in European patent application 08 004 373.0 filed on 10 Mar. 2008, page 5, lines 15-26, but any other suitable process can be used to make flexible portions.

Such flexible parts may have a structure as shown in FIGS. 2b and 2c. I.e., the flexibility may be obtained by a plurality of slits 14a, 15a, 16a, 17a. E.g., two circumferential slits may be provided in a cylindrical element along a same circumferential line where both slits are located at a certain distance from one another. A plurality of identical sets of circumferential slits 14a, 15a, 16a, 17a is provided at a plurality of distances in the longitudinal direction of the instrument, where consecutive sets are arranged at an angularly rotated position, e.g. each time 90 degrees rotated. In such an arrangement, all parts of the cylindrical element are still connected to each other.

Furthermore, if the portions 122, 123, 124, 125, 126, 127, and 128 of the first intermediate cylindrical element 102 and the portions 134, 135, and 136 of the second intermediate cylindrical element 103 that respectively form the first and second set of longitudinal steering members, as shown in FIG. 2d, are implemented as longitudinal steering elements 4 as shown in FIG. 2h, the fabrication methods described above can be used. The same applies to the longitudinal elements 2338 of FIGS. 2h and 2i. Moreover, any embodiment described in EP 2 762 058 A can be used according to the invention.

Otherwise, the longitudinal elements 4, 2338 can also be obtained by any other technique known in the art such as for example described in EP 1 708 609 A. The only restriction with respect to the construction of the longitudinal elements used in these portions is that the total flexibility of the instrument in these locations where the flexible portions coincide must be maintained.

The different co-axially arranged layers or cylindrical elements 101, 102, 103, 104, 2202, 2203 and 2204 as described above in relation to the exemplary embodiments of the steerable instruments shown in FIGS. 2d, 2e and 2f, respectively, may be produced by any of the known methods, provided that they are suitable to make a multilayer system. A multilayer system is to be understood as being a steerable instrument that comprises at least two separate sets of longitudinal elements 4, 2338 for transferring the movement of the proximal end part to the distal end part. The assembly of the different cylindrical elements can be realized in the same way as well. Preferred methods of producing the different cylindrical elements have been described in the above mentioned EP 2 762 058 A which is hereby incorporated by reference in its entirety.

In the above embodiments, the proximal portions and distal portions are constructed in a similar way. However, that need not always be the case as will become apparent hereinafter.

One of the specific problems addressed in the present document is explained with reference to FIG. 3.

Figure 3:
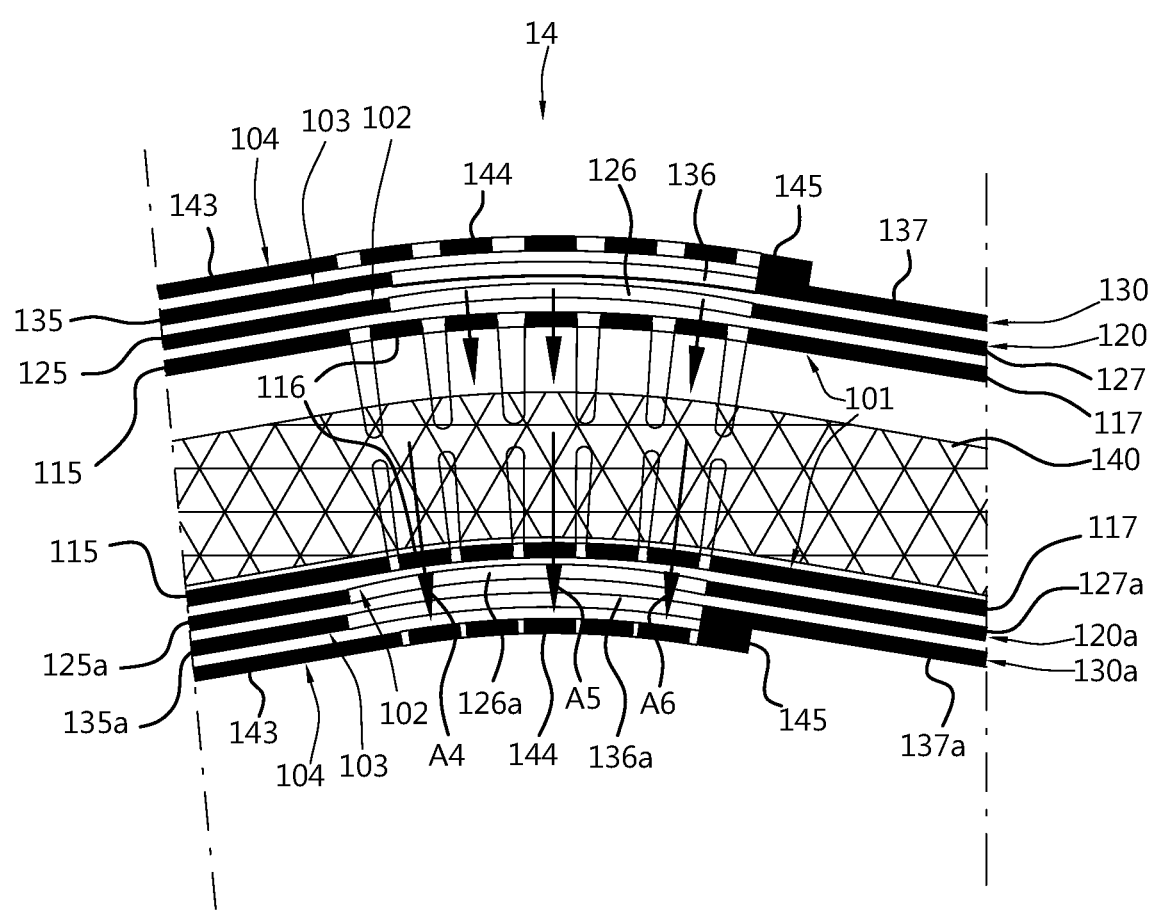
FIG. 3 shows an example of a cross section through a flexible zone of the instrument to illustrate the problem addressed by the invention.

FIG. 3 is an enlarged view of flexible zone 14 of the instrument shown in FIGS. 2d, 2e and 2f However, the same may apply to any other one of the flexible zones 15, 16, 17. Like reference numbers refer to the same elements as in these FIGS. 2d, 2e and 2f FIG. 3 shows flexible zone 14 in a bent position, like in the setup of FIG. 1. It also shows a portion of the inner cylindrical element 101 with non-flexible portion 115, flexible portion 116, and non-flexible portion 117.

Coaxially surrounding the inner cylindrical element 101 is intermediate cylindrical element 102 having several longitudinal elements 120, 120a for controlling bending of flexible zone 17 at the distal end of the instrument. A detail of one such longitudinal element 120 is shown in the upper part of FIG. 3, i.e., non-flexible portion 125, flexible portion 126, and non-flexible portion 127.

Coaxially surrounding intermediate cylindrical element 102 is cylindrical element 103 having several longitudinal elements 130, 130a which are controlling bending of flexible zone 16. A detail of one such longitudinal element 130 is shown in the upper part of FIG. 3, i.e., non-flexible portion 135 and flexible portion 136.

Reference number 137 refers to a non-flexible portion which is circumferentially surrounding portions 117 and 127.

Coaxially surrounding intermediate cylindrical element 103 is cylindrical element 104. A detail of cylindrical element 104 is shown, i.e., non-flexible portion 143, flexible portion 144, and ring 145 which is attached to portion 137 of cylindrical element 103.

The lower part of FIG. 3 shows a similar construction as the upper part. Those parts which belong to elements which are forming a circumferentially closed unit have the same reference numbers. Reference numbers 125a, 126a, 127a, 135a, and 136a, respectively, refer to similar elements as reference numbers 125, 126, 127, 135 and 136, respectively, however, they are associated with other longitudinal elements.

Inner cylindrical element 101 defines a hollow space extending from the proximal end to the distal end of the steerable instrument. The hollow space accommodates a wire 140 also extending from the proximal end to the distal end of the instrument. At the proximal end this wire 140 is attached to a suitable actuator, not shown, which may be operable manually or by a motor which is e.g. controlled by an operator or a robot, also not shown. At its distal end, the wire 140 is attached or connected to tool 2 (FIG. 1) for controlling its operation.

When flexible zone 14 is bent in the way shown in FIG. 3, the longitudinal elements in cylindrical elements 102 and 103 have moved in a longitudinal direction of the instrument such as to control bending of one of the flexible zones at the distal end of the instrument. I.e., caused by the bending shown the longitudinal elements 120 and 130 will have moved in the right direction of FIG. 3 and exert a pulling force. Consequently, because this pulling force is exerted at the outside of a virtual circular path, an inward directed force A1, A2, A3 towards the longitudinal axis of the instrument will be exerted on the longitudinal elements 120 and 130. Especially, the flexible portion 126 will have the tendency to be pushed inwardly against flexible portion 116 of cylindrical element 101. Consequently, the opposing side of cylindrical element 101 will push against flexible portion 126a of longitudinal element 120a.

Also longitudinal element 130 will be pushed inwardly, which may cause flexible portion 136 to push against flexible portion 126 of longitudinal element 120 and increase this effect on flexible portion 126a. Moreover, flexible portion 126 may be clamped on both sides by the bending movement causing friction and extra forces being necessary to control movement of the corresponding flexible zone at the distal end. Longitudinal movement of longitudinal element 130 may also be hindered by this engagement between both flexible portions 126 and 136.

At the same time, in the condition shown, a user may operate wire 140 to control movements of tool 2. Because flexible zone 14 is bent a normal force is exerted by wire 140 such that wire 140 is pushing against inner cylindrical element 101 at its inner curved position (i.e., lower part of FIG. 3). This is indicated with arrows A4, A5 and A6. In use the pulling force on wire 140 may be much higher, e.g. 10 times higher, than the pulling force on longitudinal element 120. Thus, forces A4, A5, and A6 may be much higher than forces A1, A2, and A3. So, pulling wire 140 may cause that flexible portion 126a gets clamped an can hardly move anymore. The same may be true for flexible portion 136a.

Consequently, the normal forces exerted by longitudinal elements 120, 130 and wire 140 on inner cylindrical element 101 are causing inner cylindrical element 101 to clamp longitudinal element 120a against longitudinal element 130a. This may hinder or even prevent any further longitudinal movement of longitudinal element 130a and make controlling bending of flexible zone 17 very difficult or even ineffective.

It is observed that the situation of FIG. 3 is a mere example. The actual steerable instrument may have an additional cylindrical element between the sets of longitudinal elements. Moreover, the steerable instruments may have more than two flexible zones, and, thus, more than two sets of longitudinal elements.

The present invention solves these friction problems.

The solution of the invention will best be understood with further reference to FIGS. 4-8.

Figure 4:
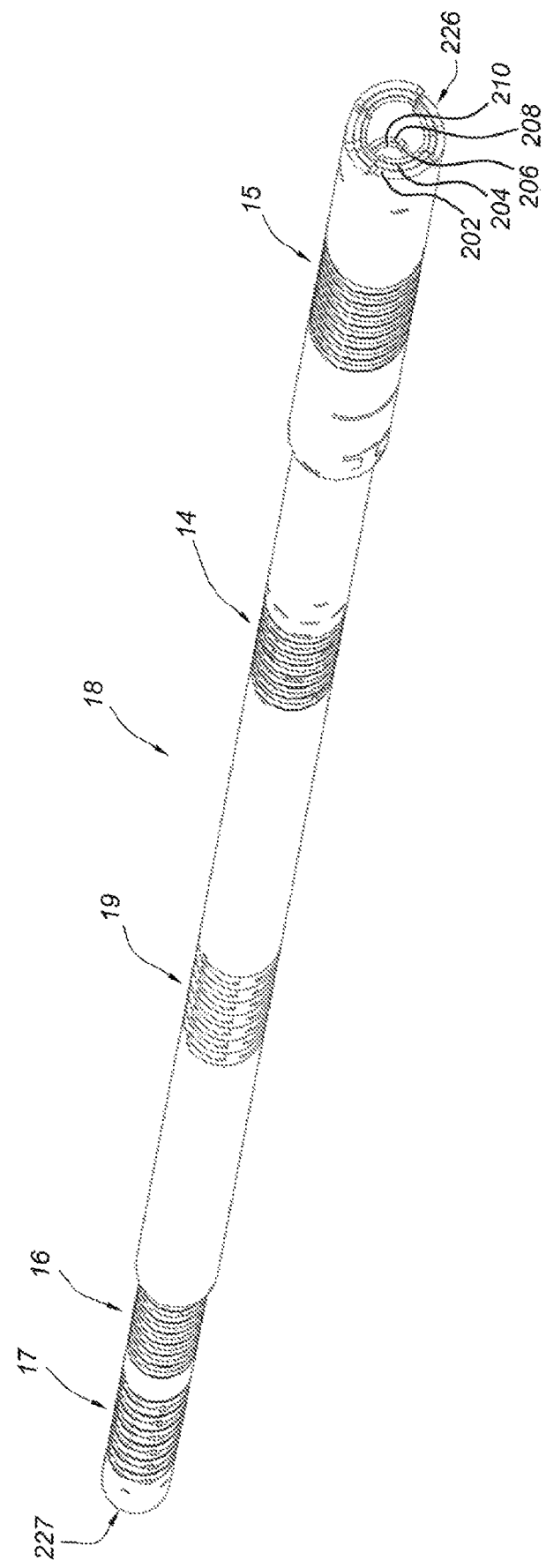
FIG. 4 shows a 3D view an exemplary embodiment of the invention.

FIG. 4 shows a 3D view of an example of a steerable instrument according to the invention. Like reference numbers refer to the same elements as in other figures. Their explanation is not repeated here. The instruments comprises five coaxial cylindrical elements 202-210. An inner cylindrical element 210 is surrounded by intermediate cylindrical element 208 which is surrounded by intermediate cylindrical element 206 which is surrounded by intermediate cylindrical element 204 which is, finally surrounded by outer cylindrical element 202. Inner intermediate cylindrical element may be made of a flexible spiraling spring. The proximal and distal ends, respectively, of the instrument are indicated with reference numbers 226 and 227, respectively.

It is observed that, here, the invention will be explained in detail with reference to "cylindrical" elements. However, it is to be understood that "cylindrical" is not to be limited to circular cross sections only. Any other suitable cross section, including elliptical, rectangular, etc. may be applied.

FIGS. 5a-5e show portions of the five coaxial cylindrical elements 202-210 at the location of the flexible zone 15 of the instrument in the disassembled state. The longitudinal dimensions of all FIGS. 5a-5e are the same such that components shown above one another in the respective FIGS. 5a-5e are, in the assembled state of the instrument, coaxially aligned with one another.

Figure 5A:
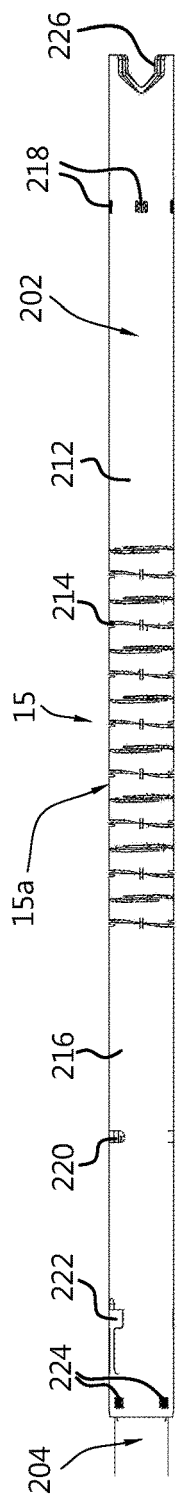
FIG. 5*a*-5*e* show five respective, coaxial cylindrical elements which, in the assembled state of the instrument, form one flexible proximal portion of the instrument.

FIG. 5a shows, at its right hand side, outer cylindrical element 202. The cylindrical element 202 is preferably made from a tube shaped element, e.g., from a suitable metal or plastic. At its left hand side, FIG. 5a shows a small portion of intermediate cylindrical element 204 in its assembled state. At its proximal end 226, the outer cylindrical element 202 comprises a rigid portion 212. Rigid portion 212 is attached to one side of a flexible portion 15a which, at its other, opposing side is attached to a rigid portion 216. Flexible portion 15a may comprise any suitable flexible means. Preferably, the flexible means are based on a plurality of hinges manufactured by cutting suitable slits and/or openings in the tube like element. That may be done by laser cutting as the person skilled in the art understands. Embodiments may include hinge types as shown and referred to in e.g. WO2009112060A1, NL2017570 and Dutch patent application NL 2019173, and U.S. Pat. App. No. 16/339,004.

Figure 5B:
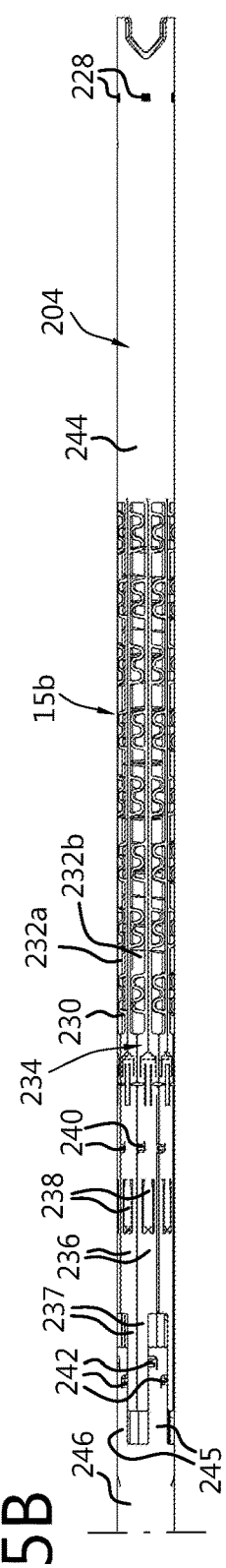

Rigid portion 212 comprises one or more slits which are shaped such as to render rigid portion 212 with one or more small lip shaped portions 218. These small lip shaped portions 218 are used for fixedly attaching rigid portion 212 to a rigid portion 244 of intermediate cylindrical element 204 by welding, as shown in FIG. 5b. The lip shaped portions 218 are so small that they will easily melt when radiated with a suitable heat source like a laser beam. The molten material of the lip shaped portions will solidify and then act as a glue between rigid portions 212 and 244 when the heat source is removed. The slit defining the welding unit with lip shaped portions 218 may be S-shaped like the slit defining lip shaped portions 294b in FIG. 8 which shows them on a larger scale. Other forms of welding unit 218 that can be easily laser melted may be used. They may be located close to end 226.

Rigid portion 216 may have one or more slit shaped openings 220 oriented circumferentially, for instance, also resulting from laser cutting. They can be used for clicking the rigid portion to a portion of another tube.

Rigid portion 216 may be provided with one or more welding units 224, which may have the same construction as welding units 218. They may be located close to the end of outer cylindrical element 202 opposing end 226. After being molten by a suitable laser beam and being solidified again they will form a solid attachment between outer cylindrical element 202 and portions of intermediate cylindrical element 204 coaxially aligned with the one or more welding units 224.

FIG. 5b shows intermediate cylindrical element 204 in detail at the location of the flexible zone 15 of the instrument. Intermediate cylindrical element 204 is preferably manufactured from a tube shaped element, e.g., from a suitable metal or plastic. All individual elements of intermediate cylindrical element 204 are the result of laser cutting suitable patterns in that tube shaped element.

At its most proximal end, intermediate cylindrical element 204 comprises a rigid portion 244. A flexible portion 15b is provided at the location of the flexible zone 15 of the instrument, which, at its proximal end, is attached to the rigid portion 244. At its distal end, flexible portion 15b is attached to longitudinal element portions 236, preferably by means of intermediate sections 234. At their distal end, each longitudinal element portion 236 is attached to an end portion 237 of smaller width. In the assembled state, these end portions 237 are able to move in a slit in the longitudinal direction, which slit is defined by extending end portions 245 of a rigid portion 246 of intermediate cylindrical element 204.

Figure 5C:
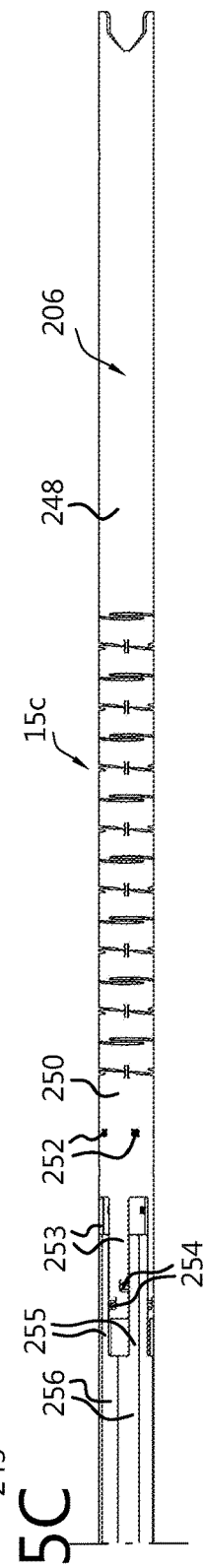

One or more small lip shaped portions 238 are formed in each longitudinal elements portion 236. They are designed such as to be meltable by a suitable laser beam in order to weld each longitudinal element portion 236 to a corresponding longitudinal element portion 256 in intermediate cylindrical element 206 (FIG. 5c). The lip shaped portions 238 can be bent inwardly to bring them closer to corresponding longitudinal element portions 256 during the welding operation and, thus, guarantee a better welding. By this arrangement, the distance of portions of the "same" longitudinal elements to the longitudinal axis can be changed such as to cause an amplification/attenuation effect of a bending movement of flexible zone 15 to a corresponding flexible zone at the distal end of the instrument to which these longitudinal elements are attached, as will be evident to persons skilled in the art.

Flexible portion 15b may comprise a plurality of sets 232a, 232b of thin wires. Each set 232a, 232b of thin wires forms a portion of a single longitudinal element. At their proximal end, each set 232a, 232b is attached to rigid portion 244 and at their distal end to one intermediate section 234. Adjacent sets 232a, 232b are separated by suitable spacers 230, e.g. M-shaped spacers as shown in FIG. 5b, and as explained in detail in patent application PCT/NL2015/050798. The two wires of each set 232a, 232b are separated by a thin slit, e.g., resulting from laser cutting. Thus, the portion of a longitudinal element in flexible portion 15b can be said to be more flexible than it would be without separation into two wires. At the same time, applying two wires instead of a single wire with the same width strengthens the potential pulling force of the longitudinal element portion at the location of flexible zone 15. Each intermediate section 234 comprises a rope equalizer: at its proximal end, each rope equalizer is attached to two wires of a set 232a, 232b, and at its distal end to one longitudinal element portion 236. The longitudinal element portion 236, in the shown arrangement, is much wider than the wires of set 232a, 232b, and therefore much less flexible, however, it is much stronger. The intermediate section 234 may have any suitable design to operate as rope equalizer, as explained in detail in Dutch patent application NL 2019173, and U.S. Pat. App. No. 16/339.004. One longitudinal element portion 236, one rope equalizer 234 and one set 232a, 232b of thin wires together form a part of a single longitudinal element of a first set of longitudinal elements. This first set of longitudinal elements is operated by a user who bends flexible zone 15 and, thus, causes the individual ones of the longitudinal elements of the first set of longitudinal elements to move in the longitudinal direction. Some of them will exert a longitudinal pulling force whereas others will exert a longitudinal pushing force depending on the bending direction of flexible zone 15. Thus, bending of flexible zone 15 causes a bending movement of a corresponding flexible zone (in the example of FIG. 1, that is flexible zone 17) at the distal end of the instrument to which the longitudinal elements of the first set of longitudinal elements are attached.

Close to its most proximal end, intermediate cylindrical element 204 is provided with one or more melting units 228 e.g. with one or more lip shaped portions that can be easily molten, e.g. by a laser beam, to attach intermediate cylindrical element 204 to intermediate cylindrical element 206 located inside intermediate cylindrical element 204 by welding.

During assembling the instrument, intermediate cylindrical element 204 is inserted into outer cylindrical element 202. In use all adjacent sets 232a, 232b of wires, and all adjacent longitudinal element portions 236 should be unconnected such that they may move in the longitudinal direction in an independent way. However, when inserting intermediate cylindrical element 204 into outer cylindrical element 202 in a state where all these portions of the longitudinal elements in intermediate cylindrical element 204 would already be unconnected, this would result in a complex and time consuming manufacturing process because the original shape of the cylindrical elements would be lost. Therefore, adjacent portions of adjacent longitudinal elements are still attached to one another during the assembling process by so-called "break islands". E.g. adjacent longitudinal element portions 236 are still attached to one another by one or more break islands 240. They may have the same construction as break islands 280 in FIG. 7b which are shown on a larger scale. i.e., break islands 240 may have the form of a circle and are attached to two adjacent longitudinal element portions 236 by means of very thin bridges that can be easily broken. Once the instrument is completely assembled, adjacent longitudinal elements are forced to move longitudinally relative to one another to such an extent that at least one of these thin bridges breaks. So, the bridges of break islands 240 should be designed such that they break before the longitudinal forces exerted on the adjacent longitudinal elements permanently deforms any portion of the adjacent longitudinal elements themselves. Such break islands are described in detail in PCT/NL/2014/050837 which is incorporated here by reference in its entirety. Any of the break islands shown in PCT/NL/2014/050837 may be applied here.

Before and during assembling the instrument the end portions 237 are still attached to extending end portions 245 of rigid portion 246 by break islands 242. Also these break islands are designed to break during first use of the instrument when end portions 237 will move relative to extending end portions 245. Break islands 242 may have a similar designs as break islands 240. However, they may have any other suitable design as disclosed in PCT/NL/2014/050837.

FIG. 5c shows a portion of intermediate cylindrical element 206 in detail at the location of flexible zone 15. In this zone 15, intermediate cylindrical element 206 comprises a flexible portion 15c. At its proximal side, the flexible portion 15c is attached to a rigid portion 248 and at its distal; side to a rigid portion 250. Rigid portion 250 is provided with several extending end portions 253 extending in the distal direction. Flexible portion 15c, preferably, comprises a plurality of hinges that can be easily made by laser cutting a suitable pattern into the cylindrical element 206, as has been explained with reference to flexible portion 15a (FIG. 5a).

At the left hand side, FIG. 5c shows that intermediate cylindrical element 206 is provided with several adjacent portions 256 of longitudinal elements. In the shown embodiment, adjacent portions 256 are separated by small longitudinal slits resulting from laser cutting. So, portions 256 can independently move in a longitudinal direction. As mentioned above, each longitudinal element portion 256 is welded to a corresponding one of the longitudinal element portions 236 by melting lip shaped portions 238 (FIG. 5b) such as to form single longitudinal elements of which portions are arranged at different distances to the longitudinal axis of the instrument.

At their proximal ends, these portions 256 comprise thinner extending end portions 255. These extending end portions, thus, define longitudinal openings in which extending end portions 253 are located. Before and during assembling the instrument two adjacent extending end portions 255 are still attached to one extending end portion 253 located between them by means of break islands 254. During first use of the instrument, as explained above, these break islands 254 will break and the longitudinal elements associated with portions 256 are free to move independently in the longitudinal direction. Any of the break islands shown in PCT/NL/2014/050837 may be applied here.

Rigid portion 250 is provided with one or more welding units 252 that may be shaped like welding units 218 and can be easily molten, e.g. by a laser beam, to attach intermediate cylindrical element 206 to a suitable portion of intermediate cylindrical element 208 located inside intermediate cylindrical element 206.

Figure 5D:
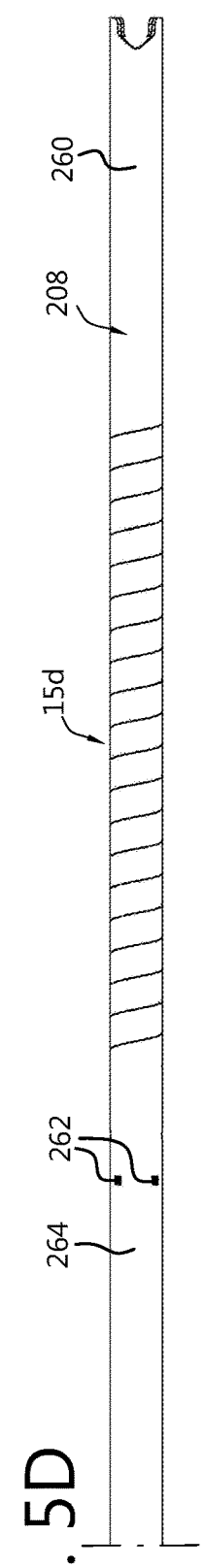

FIG. 5d shows intermediate cylindrical element 208 in detail at the location of flexible zone 15. In that zone 15, intermediate cylindrical element 208 is provided with a flexible portion 15d. Flexible portion 15d, as shown, may be made by a simple spiral shaped slit resulting from laser cutting and extending along a certain length of intermediate cylindrical element 208. At its proximal end, flexible portion 15d is attached to a rigid portion 260. At its distal end, flexible portion 15d is attached to a rigid portion 264. Rigid portion 264 comprises one or more welding units 262 that may be shaped like welding units 218 and can be easily molten, e.g. by a laser beam, to attach intermediate cylindrical element 208 to a suitable portion of inner cylindrical element 210 located inside intermediate cylindrical element 208.

Figure 5E:
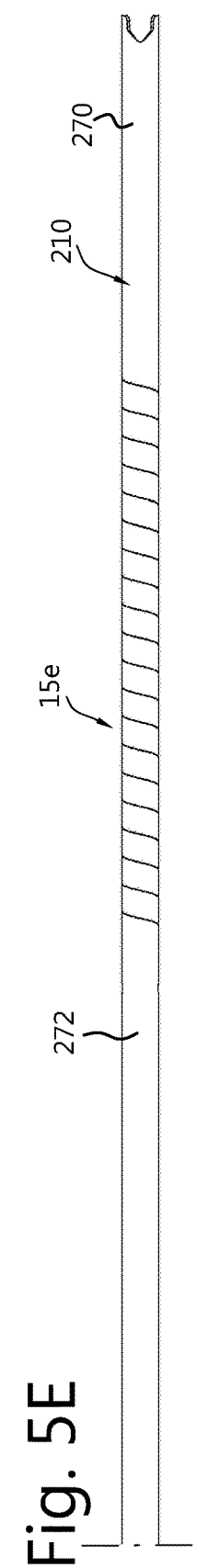

FIG. 5e shows inner cylindrical element 210 in detail at the location of flexible zone 15. In that zone 15, inner cylindrical element 210 is provided with a flexible portion 15e. Flexible portion 15e, as shown, may be made by a simple spiral shaped slit resulting from laser cutting and extending along a certain length of inner cylindrical element 210. At its proximal end, flexible portion 15e is attached to a rigid portion 270. At its distal end, flexible portion 15e is attached to a rigid portion 272.

The outer and inner diameters of the inner cylindrical element 210, the intermediate cylindrical elements 204, 206, 208 and outer cylindrical element 202 are selected such that when they are inserted into each other to form the instrument shown in FIG. 4 the respective mutual clearances between them is so small that adjacent cylindrical elements can easily move relative to one another in the longitudinal direction but that mutual radial play is kept at a minimum. The mutual clearances may be in a range of 0.02 to 0.1 mm. The thickness of the cylindrical elements may be in a range of 0.1-2.0 mm, preferably 0.1-1.0 mm, more preferably 0.1-0.5 mm, and most preferably 0.2-0.4 mm. The diameters of the cylindrical elements may be in a range of 0.5-20 mm, preferably 0.5-10 mm, more preferably 0.5-6 mm.

FIGS. 6a-6d show details of intermediate cylindrical elements 204, 206 and 208, and inner cylindrical element 210, respectively, at the location of flexible zone 14. FIGS. 7a and 7b, respectively, show parts of FIGS. 6a and 6b, respectively, on an enlarged scale for better understanding of the invention.

Figure 6A:
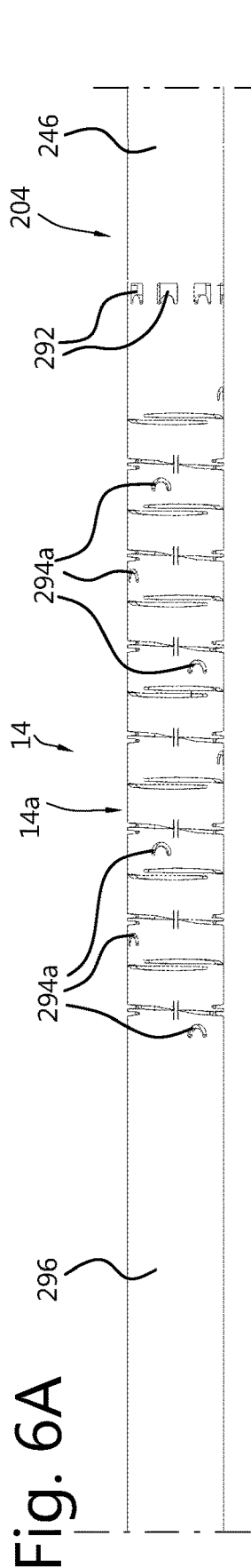
FIG. 6*a*-6*d* show four respective, coaxial cylindrical elements which, in the assembled state of the instrument, form one other flexible proximal portion of the instrument.
Figure 7A:
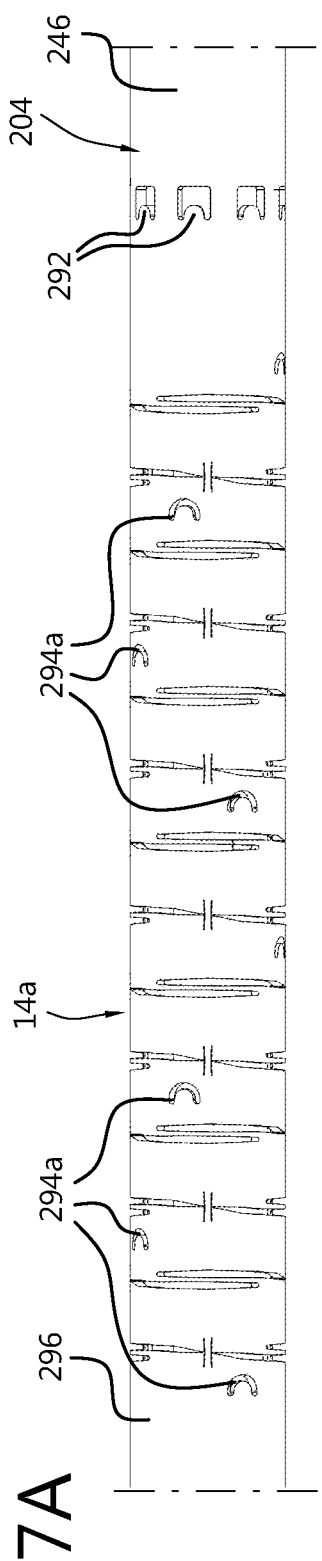
FIGS. 7*a* and 7*b*, respectively, show details of the cylindrical elements of FIGS. 6*a* and 6*b*, respectively.
Figure 7B:
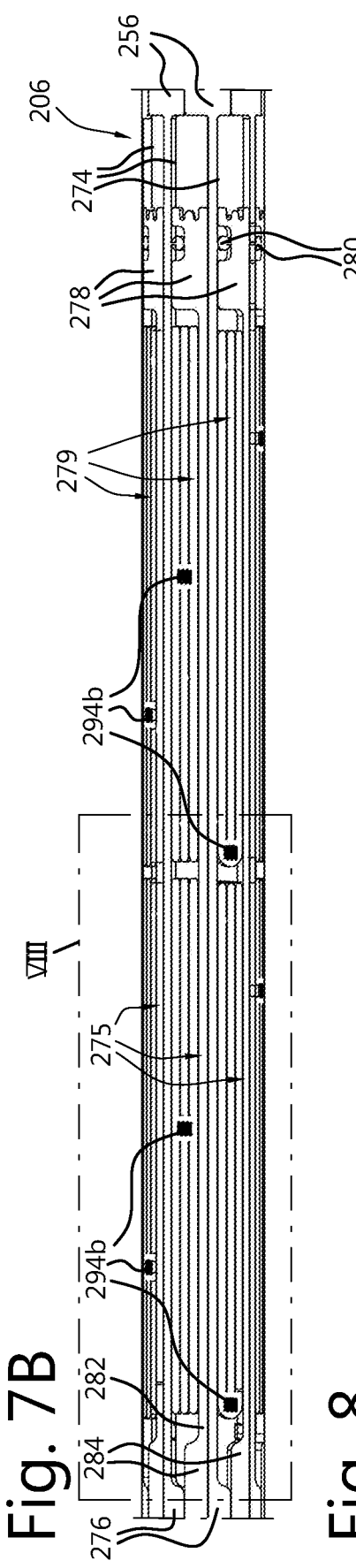

FIG. 6a, which is the extension of FIG. 5b in the distal direction of the instrument, shows rigid portion 246 at the right hand side. The distal end of rigid portion 246 is attached to one end of a flexible portion 14a located in flexible zone 14. At its other end the flexible portion 14a is attached to a rigid portion 296. Flexible portion 14a can be made of similar hinges as in flexible portions 15a, 15c, 15d, and 15c.

At several locations, flexible portion 14a is provided with small lip shaped portions 294a that are used as welding units as will become apparent hereinafter.

Rigid portion 246 is shown to be provided with one or more lip shaped portions 292. They are used as welding units, as will be further explained below.

Figure 6B:
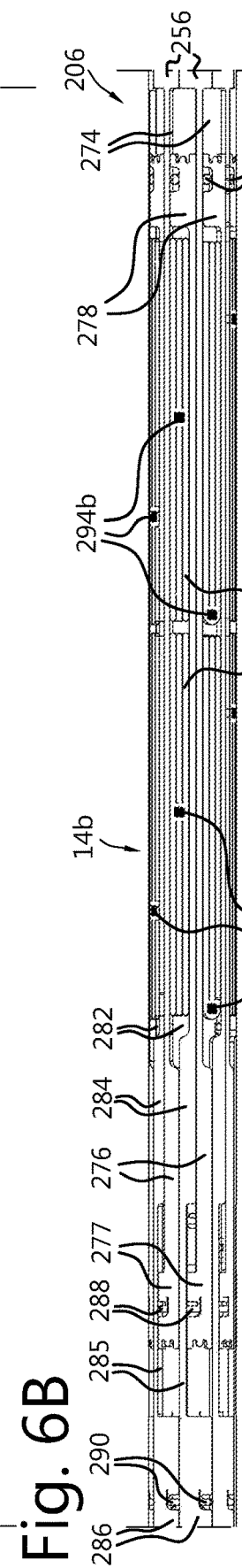

FIG. 6b, which is the extension of FIG. 5c in the distal direction of the instrument, shows further details of intermediate cylindrical element 206. At the right hand side, FIG. 6b shows the plurality of longitudinal element portions 256. At their distal end, each one of them narrows, or tapers, into a longitudinal element portion 274 of small width. Therefore, these longitudinal element portions 274 can be conceived to be thin wires which are very flexible and can be bent easily. Each one of these longitudinal element portions 274 extend along the entire length of flexible zone 14. At their distal end, each one of the longitudinal element portions 274 broadens into a wider longitudinal element portion 276.

Adjacent longitudinal element portions 274, at their proximal ends, are arranged at a predetermined distance such that open spaces are defined between them. In each such open space, a pad shaped portion 278 is located. Each pad shaped portion 278 acts as a spacer to keep adjacent longitudinal element portions 274 apart and prevent them from moving tangentially in use. The pad shaped portions 278 are the starting portions of respective longitudinal elements of a second set of longitudinal elements. Each one of the pad shaped portions 278 is attached to the rigid portion 246 of intermediate cylindrical element 204 (FIGS. 6a and 7a), preferably by means of the welding units 292. Moreover, before and during assembling the instrument, each one of the pad shaped portions 278 is still attached to one (or more) of the adjacent longitudinal element portions 274 by means of one or more break islands 280. During first use of the instrument, as explained above, these break islands 280 will break and the respective pad shaped portions 278 are free to move independently in the longitudinal direction in the open space between adjacent longitudinal element portions 274. Any of the break islands shown in PCT/NL/2014/050837 may be applied here.

Each one of the pad shaped portions 278, at their distal side, narrows into a longitudinal element portion 282. Therefore, these longitudinal element portions 282 can be conceived to be thin wires which are very flexible and can be bent easily. The longitudinal element portions 282 run longitudinally in parallel to the longitudinal element portions 274 of the first set of longitudinal elements at the location of flexible zone 14. At their distal sides, the longitudinal element portions 282 broaden into longitudinal element portions 284. These longitudinal element portions 284, at a certain further distal location, narrow into longitudinal element portions 285 having smaller widths and defining open spaces between adjacent longitudinal element portions 285.

Pad shaped portions 277 are located within these latter open spaces. These pad shaped portions 277 act as spacers to keep the longitudinal element portions 285 apart and prevent them from moving tangentially. Each one of the pad shaped portions 277 forms the end unit of one longitudinal element portion 276 to which they are attached. Moreover, each one of the pad shaped portions 277 is attached to, preferably by laser welding, one longitudinal element portion 310 located in intermediate cylindrical element 208 (see further hereinafter).

At their distal end, each one of the longitudinal element portions 285 broaden into wider longitudinal element portions 286 which are adjacent to one another and, preferably, only separated by a small slit such that tangential movement of longitudinal element portions 286 is prevented. Before and during assembling the instrument, these longitudinal element portions 286 are still attached to each other by means of break islands 290. During first use of the instrument, as explained above, these break islands 290 will break and the respective longitudinal element portions 286 are free to move independently in the longitudinal direction. Any of the break islands shown in PCT/NL/2014/050837 may be applied here.

In the arrangement shown in FIG. 1, the longitudinal elements associated with the longitudinal element portions 286 will be attached to flexible zone 16. Consequently, if a user bends flexible zone 14 also flexible zone 16 will bend. If the longitudinal elements associated with longitudinal element portions 286 would be straight along their entire length such bendings would be opposite to each other, as the person skilled in the knows. I.e., e.g., bending rigid portion 246 (FIG. 6a) downward as seen in the surface of the drawing of FIG. 6a would cause the distal side of flexible zone 16 to move upward in that same surface. As shown in FIG. 6b, however, towards the distal direction, the adjacent longitudinal element portions 286 are arranged in a spiral path. Depending on the amount of spiraling towards the distal end, in this way the distal end side of flexible zone can be caused to move in any pre-determined other space angle. In FIG. 1, the situation is shown where the distal end side of flexible zone 16 is also moved downward in a surface if rigid portion 246 is moved downward in that surface.

In the embodiment shown in FIGS. 6b and 7b, in flexible portion 14b, the plurality of longitudinal element portions 274 of the first set of longitudinal elements and the plurality of longitudinal element portions 282 of the second set of longitudinal elements are arranged as follows:

They are grouped in sets of one longitudinal element portion 274 and one longitudinal element portion 282 contacting each other in the longitudinal direction without being attached to each other.

A total of eight such sets are shown in FIGS. 6b and 7b. Between two adjacent sets there is a space filled with one or more tangential spacers 275, 279 (shown on an enlarged scale in FIG. 7b, and also FIG. 8).

Figure 8:
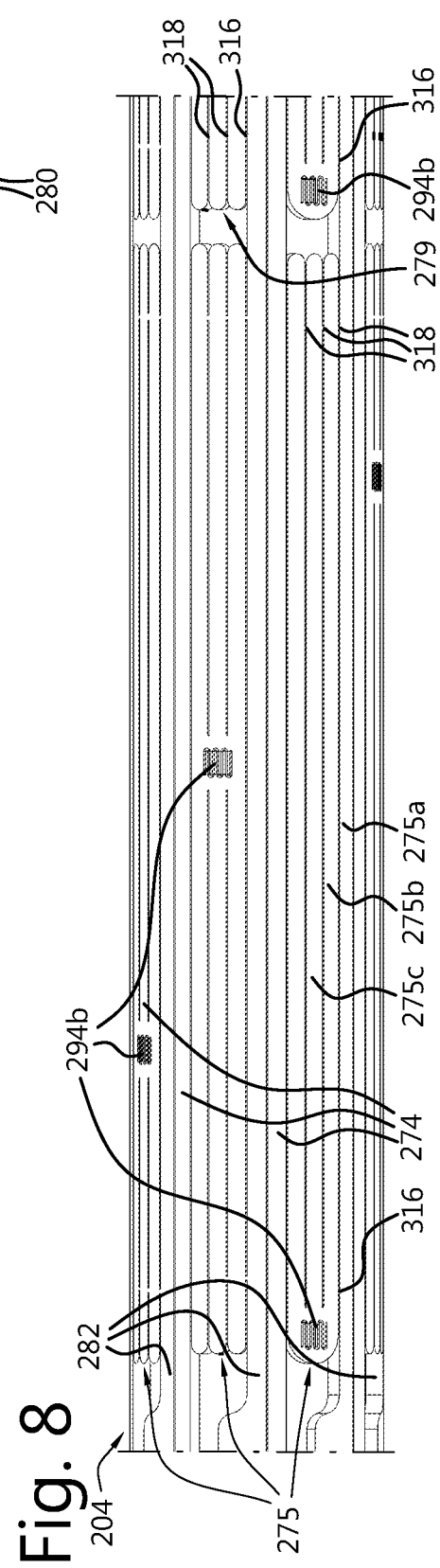
FIG. 8 shows an enlarged portion of the cylindrical element of FIG. 7*b*.

In the shown embodiment, each tangential spacer 275 comprises three separate wire shaped units 275a, 275b, 275c (FIG. 8). The wire shaped units 275a, 275b, 275c are arranged in parallel to one another in the longitudinal direction. They are separated from one another by small slits resulting from laser cutting. They are tangentially attached to one another by bridges at one or more locations such that they can only move as a single unit in the longitudinal direction. Those bridges can be located anywhere along the longitudinal direction. At the location of these bridges (or at any other suitable location) the spacer 275 is provided with welding units 294b which may be small lip shaped portions, as will be explained hereinafter. These welding units 294b may have any other suitable shape, e.g. a single lip. There may be more or less than three such wire shaped units 275a, 275b, 275c.

Before and during assembling the instrument, the spacer 275 is still attached to adjacent longitudinal element portion 282 and/or longitudinal element portion 274 by means of one or more break islands 316. Also, the one or more wire shaped units 275a, 275b, 275c may, then, still be attached to one another by means of one or more break islands 318. These break islands may be simple small bridges that can be easily broken. During first use of the instrument, as explained above, these break islands 316 will break and the respective spacers 275 are separated from adjacent longitudinal element portion 282 and/or longitudinal element portion 274. At the same time the break islands 318 will break. Any other embodiment of the break islands shown in PCT/NL/2014/050837 may be applied here instead.

As shown, spacers 279 may be constructed in the same way as spacers 275.

Once intermediate cylindrical element 206 is inserted into intermediate cylindrical element 204 such that flexible portions 14a and 14b are aligned, each welding unit 294a in flexible portion 14a is welded to one welding unit 294b on one spacer 275, 279. There may be more than one welding connection between each spacer 275, 279 and flexible portion 14a but that will reduce the flexibility of flexible zone 14. The welding between each spacer 275, 279 and flexible portion 14a will be performed such that some extra material, originating from the lip shaped portions of welding units 294a, 294b remains behind between the spacer 275, 279 and the flexible portion 14a at the location of the welding units 294a, 294b. This extra material resulting from the welding action causes each spacer 275, 279 to have a greater height in the radial direction at the welding location than the height of the adjacent longitudinal element portions 274, 282, as seen in the radial direction. So, the spacers 275, 279 also act as radial spacers. Thus, even in the bending condition of flexible zone 14, the material of flexible portions 14a and 14c are kept at a certain minimum distance which is larger than the height of the longitudinal element portions 274, 282. I.e., a cage is formed in which the longitudinal element portions 274, 282 can freely move in the longitudinal direction without being clamped between flexible portions 14a and 14c. The additional height of the radial spacers, as seen in the radial direction, is preferably in a range of 1-40%, more preferably 1-30%, and most preferably 1-15% of the height of the longitudinal element portion 274, 282.

In an alternative embodiment, the spacers 275, 279 are attached to intermediate cylindrical element 208, e.g., by means of laser welding, to form such radial spacers. In such an embodiment, the attachment is made before intermediate cylindrical elements 206 and 208 are inserted together into intermediate cylindrical element 204. After that, the welding units 294a may be welded to the radial spacers 275, 279 too.

In a further alternative, both intermediate cylindrical elements 206 and 208 are inserted into intermediate cylindrical element 204 and coaxially aligned as required. Then, welding units 294a are irradiated so intense with a laser beam that both the welding units 294a and the underlying welding units 294b will melt such that the radial spacers 275, 279 are attached to both intermediate cylindrical elements 206 and 208.

By forming cages having side walls with a larger height in the radial direction than the height of the longitudinal element portions 274, 282 the problem of the prior art as explained with reference to FIG. 3 is solved. However, it is observed that this problem is also greatly reduced by arranging the flexible longitudinal element portions 274, 282 located in flexible zone 14 of all sets of longitudinal elements in the same single cylindrical element. I.e., such flexible portions of longitudinal elements of different sets of longitudinal elements are no longer arranged on top of each other, potentially with material of a flexible portion in between, which prevents the situation shown in FIG. 3 from occurring.

Figure 6C:
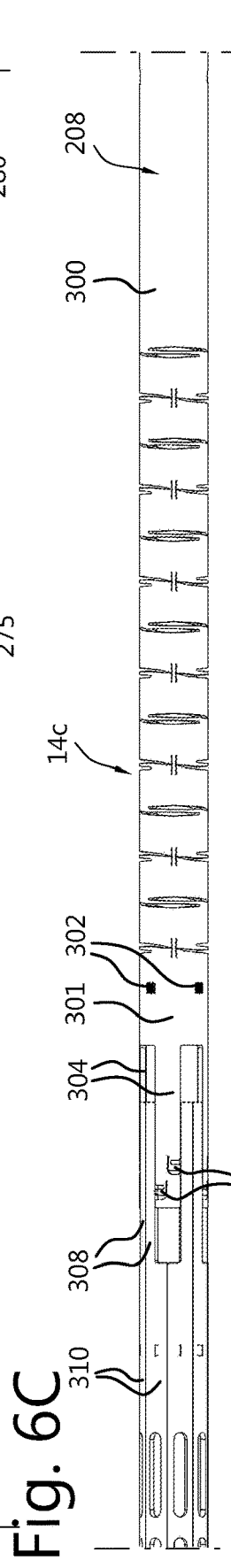

FIG. 6c shows a portion of intermediate cylindrical element 208 in detail at the location of flexible zone 14. In this zone 14, intermediate cylindrical element 208 comprises a flexible portion 14c. At its proximal side, the flexible portion 14c is attached to a rigid portion 300 and at its distal side to a rigid portion 301. Rigid portion 301 is provided with several extending end portions 304 extending in the distal direction. Flexible portion 14c, preferably, comprises a plurality of hinges that can be easily made by laser cutting a suitable pattern into the cylindrical element 208, as has been explained with reference to flexible portion 15a (FIG. 5a).

At the left hand side, FIG. 6c shows that intermediate cylindrical element 208 is provided with several adjacent portions 310 of longitudinal elements. In the shown embodiment, adjacent portions 310 are separated by small longitudinal slits resulting from laser cutting. So, portions 310 can move independently in the longitudinal direction. Each longitudinal element portion 310 is welded, e.g. by laser welding, to a corresponding one of the pad shaped portions 277 (FIG. 6b) such as to form single longitudinal elements of which portions are arranged at different distances to the longitudinal axis of the instrument.

At their proximal ends, these portions 310 comprise thinner extending end portions 308. These extending end portions 308, thus, define longitudinal openings in which extending end portions 304 are located. Before and during assembling the instrument two adjacent extending end portions 308 are still attached to one extending end portion 304 located between them by means of break islands 306. During first use of the instrument, as explained above, these break islands 306 will break and the longitudinal elements associated with portions 310 are free to move independently in the longitudinal direction. Any of the break islands shown in PCT/NL/2014/050837 may be applied here.

Rigid portion 301 is provided with one or more welding units 302, e.g., in the form of lip shaped portions that can be easily molten, e.g. by a laser beam, to attach intermediate cylindrical element 208 to a suitable portion of intermediate cylindrical element 210 located inside intermediate cylindrical element 208.

Figure 6D:
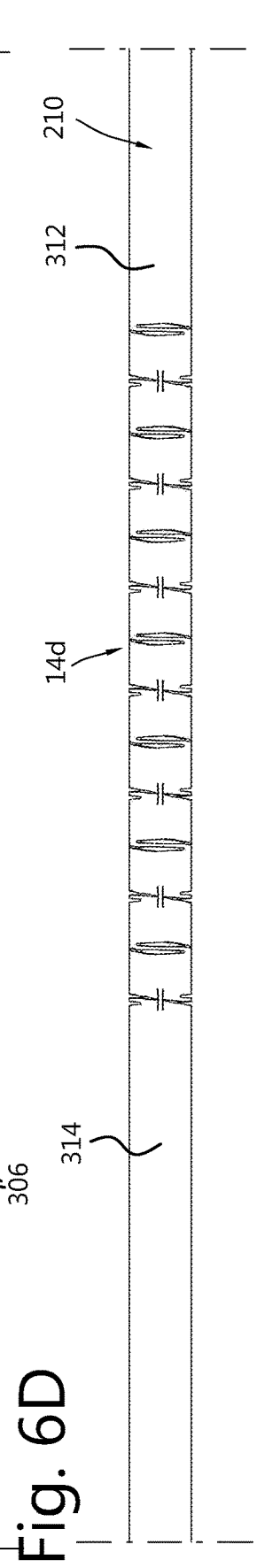

FIG. 6d shows inner cylindrical element 210 in detail at the location of flexible zone 14. In that zone 14, inner cylindrical element 210 is provided with a flexible portion 14d. Flexible portion 14d, as shown, may be made in a similar way as flexible portion 14a by laser cutting a suitable slit pattern in cylindrical element 210. However, alternatively, it may be made by a simple spiral shaped slit resulting from laser cutting and extending along a certain length of inner cylindrical element 210, or any other technique. At its proximal end, flexible portion 14d is attached to a rigid portion 312. At its distal end, flexible portion 14d is attached to a rigid portion 314.

Figure 9A:
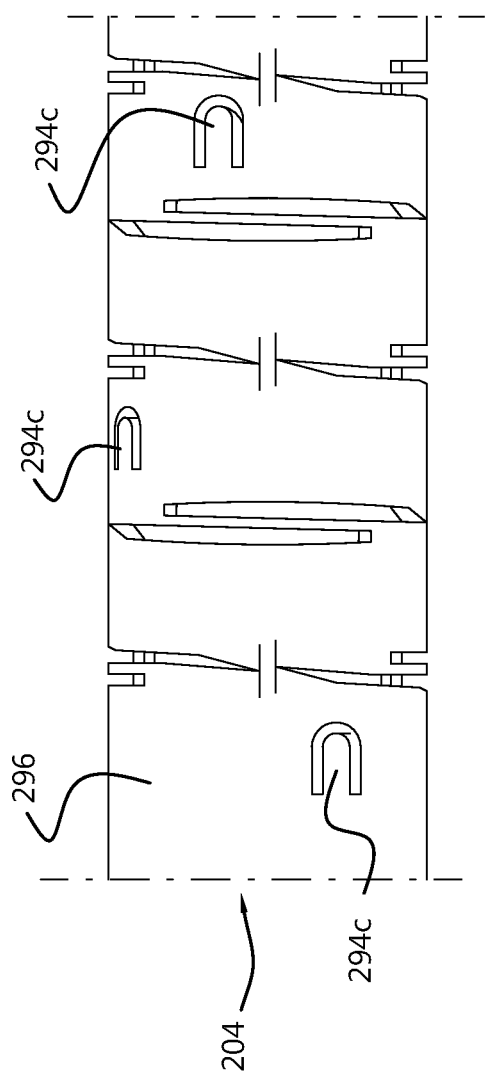
FIGS. 9A, 9B, and 10 show schematic drawings of a further embodiment of the invention in which inwardly bent lip shaped portions are used.
Figure 9B:
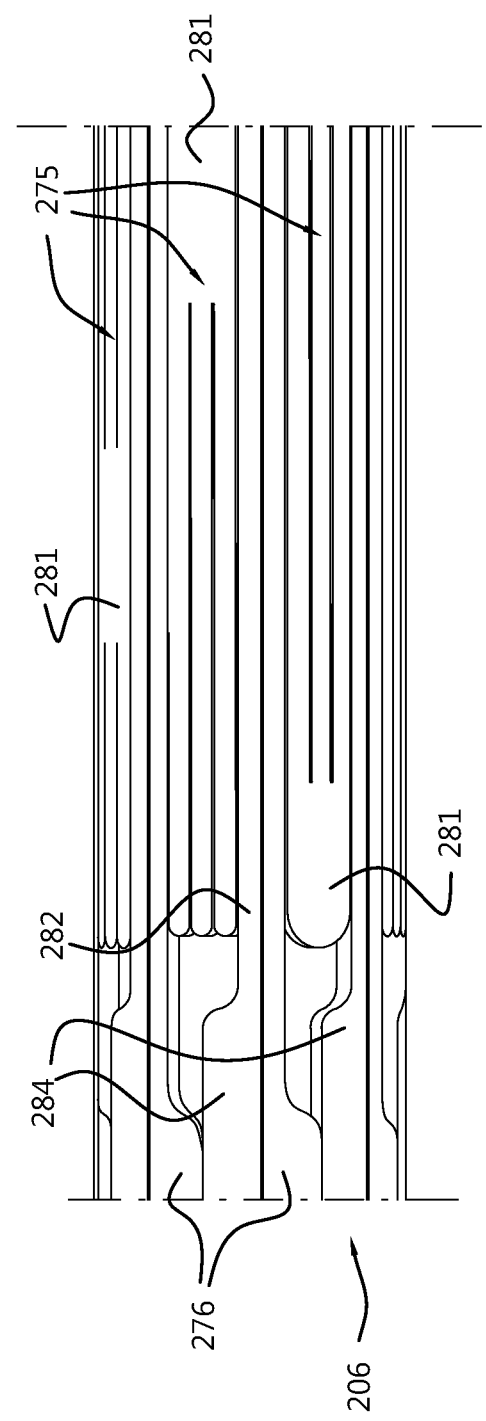
Figure 10:
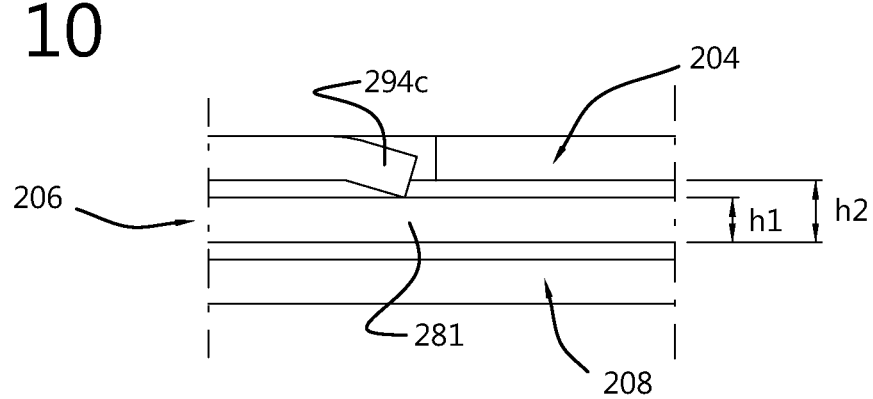

FIGS. 9A, 9B and 10 show a further embodiment of an implementation of radial spacers. In the embodiment of these figures, as shown in FIG. 9A, the lip shaped portions 294a in intermediate cylindrical element 204 are substituted by lip shaped portions 294c that need not be used in a welding process but will be bent inside during manufacturing as will be explained hereinafter.

As shown in FIG. 9B, spacers 275, 279 are no longer provided with welding units 294b but, optionally at the locations of the welding units 294b, with radial spacer portions 281. This is better shown in FIG. 10 which shows a cross section in the longitudinal direction through the instrument at a location of such a radial spacer portion 281. FIG. 10 shows the cross section through portions of intermediate cylindrical elements 204, 206, 208 in the state where they are inserted into each other.

Once intermediate cylindrical element 206 is inserted into cylindrical element 204, lip shaped portion 294c is bent inwardly such that it remains in an inward bent position and touches one radial spacer portion 281. Thus, at the location of the bent lip shaped portion 294c a fixed radial space between intermediate cylindrical elements 204 and 206 is created. FIG. 10 indicates that intermediate element 206 at the location of radial spacer portion 281 has a height h1 as measured from its inside surface to its outside surface. Because of bent lip shaped portion 294c there is a distance h2 between the inside surface of cylindrical element 206 and the inside surface of cylindrical element 204, where h2>h1. Stated differently, lip shaped portion 294c is bent inside over a radial distance of h2−h1. Thus, a well defined radial space is created for the longitudinal element portions 282 arranged alongside the spacers 275, 279 which supports free movement of these longitudinal element portions 282 in the longitudinal direction even in situations where the total instrument is bent in flexible zone 14.

Lip shaped portions 294c may be bent such that height h2 is in a range of 1-40%, more preferably 1-30%, and most preferably 1-15% more than height h1.

In an embodiment, welding units 294b are still provided on intermediate cylindrical element 206, and lip shaped portions 294c are welded to such welding units after these lip shaped portions 294c have been bent inwardly. In this way, spacers 275, 279 are prevented from freely floating which may provide the instrument with more stability.

There is no limit as to the numbers of lip shaped portions 294c used to create a well defined distance of h2−h1 between intermediate cylindrical elements 204 and 206 at some locations alongside the longitudinal element portions 282.

Figure 11A:
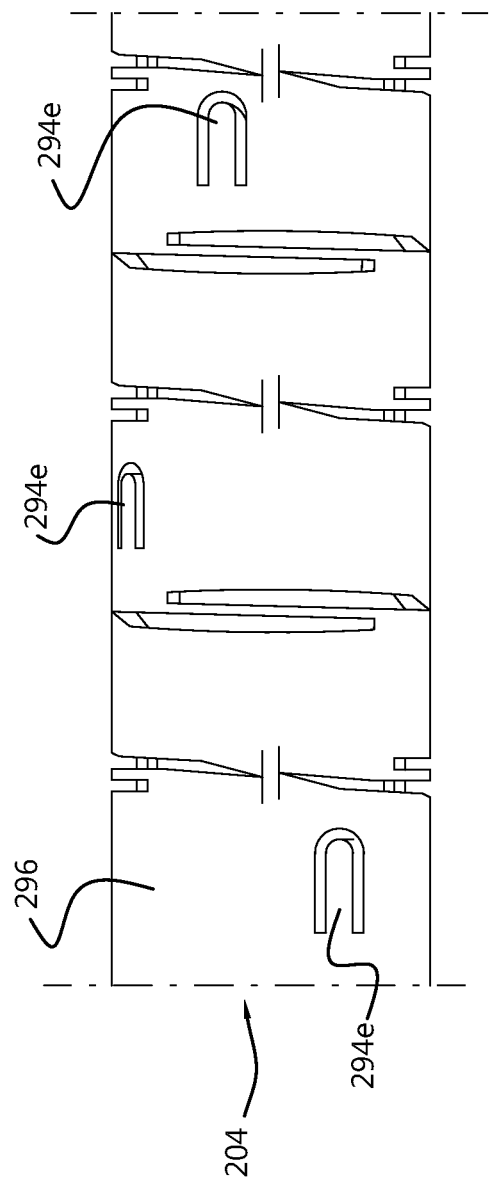
FIGS. 11A, 11B, and 12 show schematic drawings of a still further embodiment of the invention in which inwardly bent lip shaped portions are used.
Figure 11B:
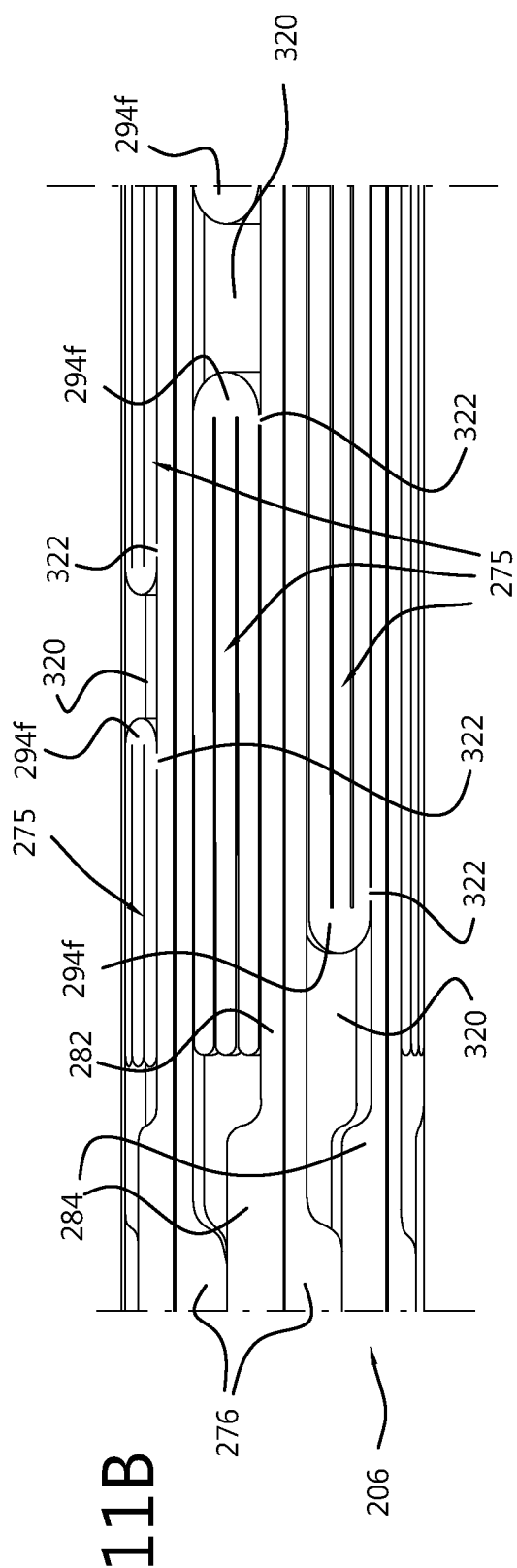
Figure 12:
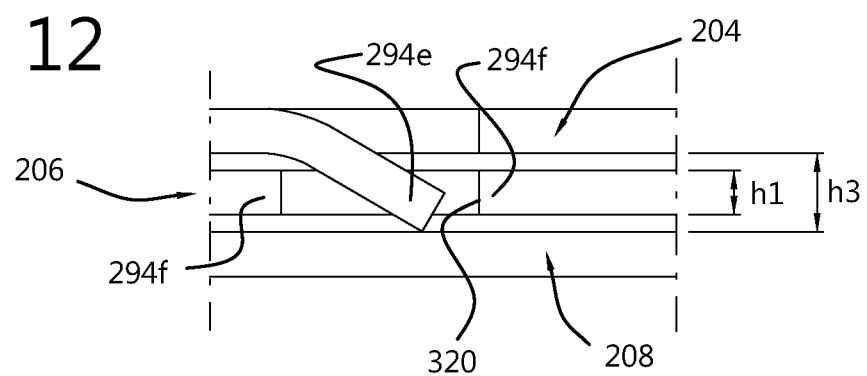

FIGS. 11a, 11b and 12 show a still further embodiment. Intermediate cylindrical element 204 is provided with lip shaped portions 294e which may have a larger length in their longitudinal direction than the lip shaped portions 294c of FIGS. 9A, 9B and 10. Wire shape units 275a, 275b, 275c of one spacer 275 are held together by a spacer portion 294f. At some locations, adjacent longitudinal element portions 282 are not spaced apart by spacers 275, 279 but by a free space 320.

Once intermediate cylindrical element 206 is inserted into cylindrical element 204, lip shaped portions 294e are located above a free space 320. Each lip shaped portion 294e is bent inwardly such that it remains in an inward bent position and extends through free space 320 and touches a portion of intermediate cylindrical element 208. Cf. FIG. 12 which shows a cross section of the instrument in the longitudinal direction at a location of such a free space 320 when intermediate cylindrical elements 204, 206, 208 are inserted into one another as shown.

Assuming again that intermediate cylindrical element 206 has a height h1, then, lip shaped portion 294e is bent inwardly over a distance of h3 where h3>h1. Thus, at the location of the bent lip shaped portion 294e a well defined radial space between intermediate cylindrical elements 204 and 208 is created which is larger than the height h1 of the longitudinal element portions 282. This supports free movement of them in the longitudinal direction even in situations where the total instrument is bent in flexible zone 14.

There is no limit as to the number of lip shaped portions 294e and free spaces 320 used to define locations of well defined radial spaces between intermediate cylindrical elements 204 and 208 alongside longitudinal element portions 282.

Lip shaped portions 294e may be bent such that height h3 is in a range of 1-40%, more preferably 1-30%, and most preferably 1-15% more than height h1.

Even though the lip shaped portions 294c, 294e of FIGS. 9A, 9B, 10, 11A, 11B, and 12 have been shown to be bent inwardly, in principle, radial spacers can, alternatively, be made by providing lip shaped portions in intermediate cylindrical element 208 and bending these lip shaped portions outwardly, e.g. either against portions 281 of spacers 275, 279 or through free spaces 320 against intermediate cylindrical element 204. This may however, in some cases, result in more complex manufacturing processes.

All cylindrical elements 202, 204, 206, 206, 208, 210 are, preferably, manufactured from a single cylindrical tube of any suitable material like stainless steel, cobalt-chromium, shape memory alloy such as Nitinol®, plastic, polymer, composites or other cuttable material. Alternatively, the cylindrical elements can be made by a 3D printing process. The thickness of that tube depends on its application. For medical applications the thickness may be in a range of 0.1-2.0 mm, preferably 0.1-1.0 mm, more preferably 0.1-0.5 mm, and most preferably 0.2-0.4 mm. The diameter of the inner cylindrical element depends on its application. For medical applications the diameter may be in a range of 0.5-20 mm, preferably 0.5-10 mm, more preferably 0.5-6 mm.

The slits and openings in all cylindrical elements can be made by laser cutting. The smaller slits which are made to just separate adjacent elements may have a width, preferably, in a range of 5-50 μm, more preferably 15-30 μm.

It will be clear to a person skilled in the art that the scope of the invention is not limited to the examples discussed in the foregoing, but that several amendments and modifications thereof are possible without deviating from the scope of the invention as defined in the attached claims. While the invention has been illustrated and described in detail in the figures and the description, such illustration and description are to be considered illustrative or exemplary only, and not restrictive. The present invention is not limited to the disclosed embodiments but comprises any combination of the disclosed embodiments that can come to an advantage.

For instance, the radial spacers are explained with reference to separate parts of one cylindrical element that are welded to at least one of another cylindrical element located inside said cylindrical element and another cylindrical element located outside said cylindrical element. The welding action is performed by melting a welding unit in one or more of these cylindrical elements which melting results in some material of the welding unit remaining to provide the separate parts with an additional height such that they become radial spacers. However, in principle, instead of this technique others may be used in which separate radial spacers are used which have a larger height than the longitudinal element portions itself anyway. However, the described technique has the advantage that one can start with cylindrical elements which are laser cut to render the desired patterns, followed by laser welding the welding units as explained.

The radial spacers 275, 279 are flexible. It is to be understood that the slit patterns applied to provide them with the desired flexibility is not limited to the shown examples. Slits may be defined in any suitable pattern including slits directed in the longitudinal and/or tangential direction, as well as any curved slits.

The above embodiments are shown with bendable zones 14 and 15 at the proximal end of the instrument, arranged to control bending of the bendable zones 16, 17 at the distal end by means of two sets of longitudinal elements. The bendable zones 14, 15 can be replaced by other actuating means like suitable motors arranged to control the movement of the longitudinal elements. In a further alternative, such actuating means could be constructed as a ball to which the longitudinal elements are attached. Rotating the ball will longitudinally move the longitudinal elements and, thus, control the bending of the flexible zones 16, 17.

The invention is also applicable in instruments having only one bendable zone, and thus only one set of longitudinal elements. A cage as shown accommodates two adjacent longitudinal elements, however, the invention is not restricted to this number. The number of accommodated longitudinal elements in a single cage may be one or more. There may be more than two sets of longitudinal elements, each set arranged to control bending of one flexible zone at the distal end of the instrument. The cages may be applied in non-flexible zones of the instrument as well.

Although the invention has been described with reference to cages in flexible zone 14, such cages can be applied in any other one of the flexible zones 15, 16, and 17 both at the proximal end and distal end of the instrument.

Variations to the disclosed embodiments can be understood and effected by a person skilled in the art in practicing the claimed invention, from a study of the figures, the description and the attached claims. In the description and claims, the word "comprising" does not exclude other elements, and the indefinite article "a" or "an" does not exclude a plurality. In fact it is to be construed as meaning "at least one". The mere fact that certain features are recited in mutually different dependent claims does not indicate that a combination of these features cannot be used to advantage. Any reference signs in the claims should not be construed as limiting the scope of the invention. Features of the above described embodiments and aspects can be combined unless their combining results in evident technical conflicts.

The invention claimed is:

1. A steerable instrument for endoscopic and/or invasive type of applications, such as in surgery, the instrument comprising an elongated tubular body extending in a longitudinal direction and having at least one actuation means at a proximal side of the steerable instrument and at least one bendable zone at a distal side of the steerable instrument, said at least one actuation means being arranged to control bending of said at least one bendable zone by means of at least one longitudinal element, the instrument comprising a first cylindrical element, a second cylindrical element and a third cylindrical element, the first cylindrical element surrounding the second cylindrical element and the second cylindrical element surrounding the third cylindrical element, the second cylindrical element comprising a zone with a longitudinal element portion of said at least one longitudinal element, said longitudinal element portion having a first height in a radial direction of said instrument, wherein at least one of the first cylindrical element, the second cylindrical element and the third cylindrical element comprises at least two radial spacers at mutual sides of said longitudinal element each one of said radial spacers having, at least locally, a second height in the radial direction larger than the first height.

2. The steerable instrument according to claim 1, wherein said second height is in a range of 1-40% more than the first height.

3. The steerable instrument according to claim 1, wherein said instrument comprises at least two longitudinal element portions in said zone and defining a space between them, one radial spacer being arranged in said space such as to also form a tangential spacer between said adjacent at least two longitudinal element portions.

4. The steerable instrument according to claim 1, wherein the radial spacers are flexible spacers.

5. The steerable instrument according to claim 4, wherein the radial spacers comprise a plurality of distinct portions separated by slits.

6. The steerable instrument according to claim 5, wherein the distinct portions are wire shaped units extending in the longitudinal direction and separated by the slits.

7. The steerable instrument according to claim 5, wherein the slits comprise at least one of: slit portions extending in the longitudinal direction, the slit portions extending in a tangential direction, and the slit portions having a curved shape.

8. The steerable instrument according to claim 4, wherein the radial spacers are located in the at least one bendable zone of the steerable instrument.

9. The steerable instrument according to claim 1, wherein the at least one bendable zone comprises at least a first bendable zone at its distal end and a second bendable zone at its distal end, the first bendable zone being controllable by a first set of one or more longitudinal elements of said at least one longitudinal element, and the second bendable zone being controllable by a second set of one or more longitudinal elements of said at least one longitudinal element, at least one longitudinal element of said first set and at least one longitudinal element of said second set being located in parallel between said at least two radial spacers.

10. The steerable instrument according to claim 1, wherein the radial spacers include a bent lip shaped portion.

11. The steerable instrument according to claim 10, wherein the lip shaped portion is part of the first cylindrical element and bent inwardly against a portion of said second cylindrical element adjacent said longitudinal element portion.

12. The steerable instrument according to claim 10, wherein the lip shaped portion is part of the first cylindrical element and bent inwardly against a portion of said third cylindrical element through a free space 3 in said second cylindrical element adjacent said longitudinal element portion.

13. The steerable instrument according to claim 1, wherein said second height is in a range of 1-30% more than the first height.

14. The steerable instrument according to claim 1, wherein said second height is in a range of 1-15% more than the first height.

15. A method of manufacturing a steerable instrument according to claim 1, wherein the method comprises:
providing said first cylindrical element;
inserting said second cylindrical element into said first cylindrical element and locally welding said at least two radial spacers to said first cylindrical element such as to cause said at least two radial spacers to locally obtain said second height; and
inserting said third cylindrical element into said second cylindrical element;
or:
providing said second cylindrical element;
inserting said third cylindrical element into said second cylindrical element and locally welding said at least two radial spacers to said third cylindrical element such as to cause said at least two radial spacers to locally obtain said second height; and
inserting said second cylindrical element and third cylindrical element together into said first cylindrical element;
or:
providing an assembly of said first, second and third cylindrical elements such that said third cylindrical element is inserted into said second cylindrical element and said second cylindrical element is inserted into said first cylindrical element; and
locally welding said at least two radial spacers to at least one of said first cylindrical element and said third cylindrical element such as to cause said at least two radial spacers to locally obtain said second height.

* * * * *